United States Patent
Fritch et al.

(10) Patent No.: US 7,812,176 B2
(45) Date of Patent: Oct. 12, 2010

(54) PROCESSES FOR PREPARING SUBSTITUTED N-ARYL-N'-[3-(1H-PYRAZOL-5-YL) PHENYL] UREAS AND INTERMEDIATES THEREOF

(75) Inventors: John Robert Fritch, Ramona, CA (US); Fiona M. Carleton, San Diego, CA (US); Edward A. Lally, La Jolla, CA (US); Hongmei Li, Warren, NJ (US); Bradley Teegarden, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 443 days.

(21) Appl. No.: 10/593,847

(22) PCT Filed: Jul. 21, 2004

(86) PCT No.: PCT/US2004/023880

§ 371 (c)(1),
(2), (4) Date: Aug. 2, 2007

(87) PCT Pub. No.: WO2005/103011

PCT Pub. Date: Nov. 3, 2005

(65) Prior Publication Data

US 2007/0293685 A1  Dec. 20, 2007

Related U.S. Application Data

(60) Provisional application No. 60/555,626, filed on Mar. 23, 2004.

(51) Int. Cl.
  *C07D 231/10* (2006.01)
(52) U.S. Cl. .................................. 548/377.1
(58) Field of Classification Search ............... 548/377.1
  See application file for complete search history.

(56) References Cited

U.S. PATENT DOCUMENTS

| | | | |
|---|---|---|---|
| 4,099,012 A | 7/1978 | Gschwend | |
| 4,405,644 A | 9/1983 | Kabbe et al. | |
| 4,409,231 A | 10/1983 | Stenzel et al. | |
| 4,985,352 A | 1/1991 | Julius et al. | |
| 5,077,409 A | 12/1991 | Wissner | |
| 5,128,351 A | 7/1992 | Wissner | |
| 5,523,280 A | 6/1996 | Chene et al. | |
| 5,661,024 A | 8/1997 | Kao et al. | |
| 5,885,785 A | 3/1999 | Kao et al. | |
| 5,886,044 A | 3/1999 | Widdowson et al. | |
| 5,905,080 A | 5/1999 | Duckworth et al. | |
| 5,945,382 A | 8/1999 | Cantegril et al. | |
| 5,990,133 A | 11/1999 | Gaster et al. | |
| 6,005,008 A | 12/1999 | Widdowson et al. | |
| 6,028,085 A | 2/2000 | Bromidge | |
| 6,054,472 A | 4/2000 | Armistead et al. | |
| 6,107,324 A | 8/2000 | Behan et al. | |
| 6,140,509 A | 10/2000 | Behan et al. | |
| 6,150,393 A | 11/2000 | Behan et al. | |
| 6,271,261 B1 | 8/2001 | Widdowson | |
| 6,297,261 B1 | 10/2001 | Christophersen et al. | |
| 6,358,698 B1 | 3/2002 | Weiner et al. | |
| 6,383,762 B1 | 5/2002 | Kao et al. | |
| 6,417,393 B1 | 7/2002 | Christophersen et al. | |
| 6,420,541 B1 | 7/2002 | Behan et al. | |
| 6,479,480 B1 | 11/2002 | Moyes et al. | |
| 6,479,519 B1 | 11/2002 | Astles et al. | |
| 6,531,291 B1 | 3/2003 | Kabbash et al. | |
| 6,541,209 B1 | 4/2003 | Behan et al. | |
| 6,696,475 B2 | 2/2004 | Dahl et al. | |
| 6,706,749 B2 | 3/2004 | Dahl et al. | |
| 6,784,183 B2 | 8/2004 | Lavielle et al. | |
| 6,846,919 B2 | 1/2005 | Behan et al. | |
| 7,368,539 B2 | 5/2008 | Behan et al. | |
| 2002/0025965 A1 | 2/2002 | Lavielle et al. | |
| 2002/0098548 A1 | 7/2002 | Kao et al. | |
| 2004/0102636 A1 | 5/2004 | Miller et al. | |
| 2005/0054691 A1 | 3/2005 | Potter et al. | |
| 2005/0080124 A1 | 4/2005 | Teegarden et al. | |
| 2005/0267097 A1 | 12/2005 | Pinto et al. | |
| 2006/0014705 A1 | 1/2006 | Howitz et al. | |

(Continued)

FOREIGN PATENT DOCUMENTS

CA   2135253   5/1996

(Continued)

OTHER PUBLICATIONS

Andrzejewska-Buczko et al., "Serotonin in diabetic retinopathyl", Klin Oczna Feb. 1996; 98(2):101-4 (abstract only).

(Continued)

*Primary Examiner*—Kamal A Saeed
*Assistant Examiner*—Samantha L Shterengarts
(74) *Attorney, Agent, or Firm*—Fish & Richardson P.C.; Lyle Spruce

(57) ABSTRACT

The present invention is directed to processes for the preparation of substituted phenylpyrazole ureas of Formula (I), that are useful as $5\text{-HT}_{2A}$ serotonin receptor modulators for the treatment of disease.

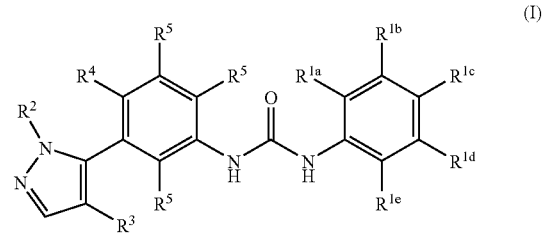

37 Claims, No Drawings

U.S. PATENT DOCUMENTS

| | | | |
|---|---|---|---|
| 2006/0063754 | A1 | 3/2006 | Edgar et al. |
| 2006/0205792 | A1 | 9/2006 | Wong et al. |
| 2006/0229335 | A1 | 10/2006 | Teegarden et al. |
| 2007/0037827 | A1 | 2/2007 | Nunes et al. |
| 2007/0072857 | A1 | 3/2007 | Teegarden et al. |
| 2007/0207994 | A1 | 9/2007 | Teegarden et al. |
| 2007/0244086 | A1 | 10/2007 | Teegarden et al. |
| 2007/0293685 | A1 | 12/2007 | Fritch et al. |
| 2008/0015223 | A1 | 1/2008 | Strah-Pleynet et al. |
| 2008/0200530 | A1 | 8/2008 | Unett et al. |
| 2009/0053306 | A1 | 2/2009 | Agarwal et al. |
| 2009/0076254 | A1 | 3/2009 | Behan et al. |
| 2009/0186895 | A1 | 7/2009 | Teegarden et al. |
| 2009/0197935 | A1 | 8/2009 | Teegarden et al. |

FOREIGN PATENT DOCUMENTS

| | | |
|---|---|---|
| EP | 1108720 A1 | 6/2001 |
| EP | 1 558 582 | 8/2005 |
| EP | 1734039 | 12/2006 |
| FR | 2 722 369 | 1/1996 |
| GB | 1147379 | 12/1967 |
| WO | WO 96/02138 | 2/1996 |
| WO | WO 96/10559 | 4/1996 |
| WO | WO 96/23783 | 8/1996 |
| WO | WO 97/03967 | 2/1997 |
| WO | WO 97/45111 | 12/1997 |
| WO | WO 98/24785 | 6/1998 |
| WO | WO 99/06354 | 2/1999 |
| WO | WO 99/32436 | 7/1999 |
| WO | WO 99/32463 | 7/1999 |
| WO | WO 99/32927 | 7/1999 |
| WO | WO 99/52927 | 10/1999 |
| WO | WO 00/57877 A1 | 10/2000 |
| WO | WO 00/64866 | 11/2000 |
| WO | WO 01/21160 | 3/2001 |
| WO | WO 01/29008 | 4/2001 |
| WO | WO 02/39987 | 5/2002 |
| WO | WO 02/051833 | 7/2002 |
| WO | WO 02/076464 | 10/2002 |
| WO | WO 03/062206 | 7/2003 |
| WO | WO 03/062206 | 1/2004 |
| WO | WO 2004/028450 | 4/2004 |
| WO | WO 2004/045118 | 5/2004 |
| WO | WO 2004/058722 | 7/2004 |
| WO | WO 2004/071426 | 8/2004 |
| WO | WO 2004/028450 | 10/2004 |
| WO | WO 2004/085433 | 10/2004 |
| WO | WO 2004/096771 | 11/2004 |
| WO | WO2005012254 | 2/2005 |
| WO | WO 2005/077345 | 8/2005 |
| WO | WO 2005/103011 | 11/2005 |
| WO | WO 2006/018662 | 2/2006 |
| WO | WO 2006/049734 | 5/2006 |
| WO | WO 2006/049941 | 5/2006 |
| WO | WO 2006/055734 | 5/2006 |
| WO | WO 2006/059149 | 6/2006 |
| WO | WO 2006/060654 | 6/2006 |
| WO | WO 2006/070394 | 7/2006 |
| WO | WO 2006/076592 | 7/2006 |
| WO | WO 2006/078610 | 7/2006 |
| WO | WO 2006/079637 | 8/2006 |
| WO | WO2006/081335 | 8/2006 |
| WO | WO 2006/086705 | 8/2006 |
| WO | WO 2006/089871 | 8/2006 |
| WO | WO 2006/095205 | 9/2006 |
| WO | WO 2006/097766 | 9/2006 |
| WO | WO 2006/100519 | 9/2006 |
| WO | WO 2006/112464 | 10/2006 |
| WO | WO 2006/116614 | 11/2006 |
| WO | WO 2007/002559 | 1/2007 |
| WO | WO 2007/026959 | 3/2007 |
| WO | WO 2007/120600 | 10/2007 |
| WO | WO 2007/129111 | 11/2007 |
| WO | WO 2007/136680 | 11/2007 |
| WO | WO 2007/136703 | 11/2007 |
| WO | WO 2007/136875 | 11/2007 |
| WO | WO 2008/027483 | 3/2008 |
| WO | WO 2008/042388 | 4/2008 |
| WO | WO 2008/054748 | 5/2008 |
| WO | WO 2009/023253 | 2/2009 |

OTHER PUBLICATIONS

Berge et al., "Pharmaceutical salts", J. of Pharmaceutical Sciences (1977) 66(1):1-19.

Cameron et al., "The effects of 5-hydroxytryptamine 5-HT2 receptor antagonists on nerve conduction velocity and endoneurial perfusion in diabetic rats", Naunyn Schmiedebergs Arch Pharmacol, Jun. 2003; 367(6):607-14.

Casey et al., "Constitutively active mutant $5HT_{2A}$ serotonin receptors: inverse agonist activity of classical $5HT_{2A}$ antagonists", Society for Neuroscience Abstracts, vol. 22, p. 699.10.

Cazzola et al., "5-HT modifiers as a potential treatment of asthma", TIPS, 2000, vol. 21, p. 13.

Chang et al., "Mechanism of the ocular hypotensive action of ketanserin", J Ocul Pharmacol., 1985 Summer; 1(2):137-47.

Cohen-Mansfield et al., "Agitated behaviors in the elderly. I. A conceptual review", J. Am. Geriatr. Soc., Oct. 1986; 34(10):711-21.

Collier et al., "Radiosynthesis and in-vivo evaluation of the pseudopeptide δ-opioid antagonist [$^{125}$I]-ITIPP(ψ)", J. Labeled Compd. Radiopharm., 1999, vol. 42, pp. S264-S266.

Collins et al., "N-Phenylamidines as Selective Inhibitors of Human Neuronal Nitric Oxide Synthase: Structure-Activity Studies and Demonstration of in Vivi Activity", *Journal of Medicinal Chemistry, American Chemical Society*, 41, No. 15, pp. 2858-2871, 1998; XP0022144154.

De Bie et al., "Modulation of airway hyperresponsiveness and eosinophilia by selective histamine and 5-HT receptor antagonists in a mouse model of allergic asthma", British Journal of Pharmacology, 1998, vol. 124:857-864.

Greene et al., Protecting Groups in Organic Synthesis, 3$^{rd}$ Edition, 1999 (Wiley).

Grunder et al., Time course of 5-HT2A receptor occupancy in the human brain after a single oral dose of the putative antipsychotic drug MDL 100,907 measured by positron emission tomography, Neuropsychopharmacology, Sep. 1997; 17(3):175-85.

Herrick-Davis et al., "Activating mutations of the serotonin 5-HT2C receptor", J. Neurochem., Sep. 1997; 69(3):1138-44.

Herrick-Davis et al., "Constitutively active 5HT2C serotonin receptor created by site-directed mutagenesis", Society for Neuroscience Abstracts, vol. 22, p. 699.18.

Higuchi et al., "Pro-drugs and Novel Delivery Systems", vol. 14 of the ACS Symposium Series; and in Bioreversible Carriers in Drug Design, ed. Edward B. Roche, American Pharmaceutical Association and Pergamon Press, 1987.

Katz et al., "Comparison of risperidone and placebo for psychosis and behavioral disturbances associated with dementia: a randomized, double-blind trial. Risperidone Study Group", J. Clin. Psychiatry, Feb. 1999; 60(2):107-15.

Koss et al., "Assessing patterns of agitation in Alzheimer's disease patients with the Cohen-Mansfield Agitation Inventory. The Alzheimer's Disease Cooperative Study", Alzheimer Dis Assoc Disord. 1997; 11 Suppl 2:S45-50.

Landolt et al., "Serotonin-2 receptors and human sleep: effect of a selective antagonist on EEG power spectra", Neuropsychopharmacology, Sep. 1999; 21(3):455-66.

Le Bas et al., "Radioiodinated analogs of EP 00652218 for the exploration of the tachykinin NK1 receptor by spect", J. Labeled Compd. Radiopharm., 2001, vol. 44:S280-S282.

Mastropasqua et al., "Ocular hypotensive effect of ketanserin in patients with primary open angle glaucoma", Acta Ophthalmol Scand Suppl., 1997 (224):24-5.

National Institutes of Health, National Heart, Lung and Blood Institute, "Insomnia" (Oct. 1995) pp. 1-4.

Pietraszek et al., "Blood serotonergic mechanisms in type 2 (non-insulin-dependent) diabetes mellitus", Thromb Res., Jun. 15, 1992; 66(6):765-74.

Prosser et al., "Selective serotonin 5-HT$_{2A}$ inverse agonists promote sleep consolidation in male Wistar rats during the normal inactive phase", #29, Arena Pharmaceuticals, Inc., APSS Meeting (Jun. 2004) 1 page.

Remington, The Science and Practice of Pharmacy, 20$^{th}$ Edition, 2000 (Lippincott Williams & Wilkins).

Satomura et al., "Sarpogrelate, a specific 5HT2-receptor antagonist, improves the coronary microcirculation in coronary artery disease", Clin. Cardiol. Jan. 2002; 25(1):28-32.

Sharpley et al., "Slow wave sleep in humans: role of 5-HT2A and 5-HT2C receptors", Neuropharmacology, Mar.-Apr. 1994; 33(3-4):467-71.

Smith et al., "Test-retest variability of serotonin 5-HT2A receptor binding measured with positron emission tomography and [18F]altanserin in the human brain, Synapse, Dec. 1998; 30(4):380-92.

Staley et al., Comparison of [(18)F] altanerin and [(18)F]durteroaltanserin for PET imaging of serotonin (2A) receptors in baboon brain: pharmacological studies, Nucl Med Biol, Apr. 2001; 28(3):271-9.

Strah-Pleynet et al., "Discovery and SAR of novel 5-HT$_{2A}$ inverse-agonists", 227 ACS National Meeting, MEDI 270, Arena Pharmaceuticals, Inc. (Mar. 2004), 1 page.

Street et al., "Olanzapine treatment of psychotic and behavioral symptoms in patients with Alzheimer disease in nursing care facilities: a double-blind, randomized, placebo-controlled trial. The HGEU Study Group", Arch Gen Psychiatry, Oct. 2000; 57(10):968-76.

Takahashi et al., "Sarpogrelate hydrochloride, a serotonin 2A receptor antagonist, reduces albuminuria in diabetic patients with early-stage diabetic nephropathy", Diabetes Res Clin Pract. Nov. 2002, 58(2):123-9.

Takenaka et al., "The effect of anplag (sarpogrelate HCl), novel selective 5-HT$_2$ antagonist on intraocular pressure in glaucoma patients", Investig Ophthalmol Vis Sci, 36(4):S724 (3390-377).

Talvik-Lotfi et al., "High 5HT2A receptor occupancy in M100907-treated schizophrenic patients", Phychopharmacology (2000) 148:400-403.

The International Classification of Sleep Disorders, Revised Diagnostic and Coding Manual, American Academy of Sleep Medicine (2001) pp. 1-336 (also includes table of contents and glossary).

Topliss, John G., "A Manual Method for Applying the Hansch Approach to Drug Design", Journal of Medicinial Chemistry, vol. 20, No. 4, pp. 463-469, 1997.

Wilson et al., "LY53857, a 5HT2 Receptor Antagonist, Delays Occlusion and Inhibits Platelet Aggregation in a Rabbit Model of Carotid Artery Occlusion", Thromb Haemost. Sep. 2, 1991; 66(3):355-60.

Winokur et al., "Acute effects of mirtazapine on sleep continuity and sleep architecture in depressed patients: a pilot study", Biol Psychiatry, Jul. 1, 2000; 48(1):75-8.

Zhu et al., "Synthesis and mode of action of [$^{125}$I]-and $^3$H-labeled Thieno -2,3-c]pyridine antagonists of cell adhesion molecule expression", J. Org. Chem., (200) 67:943-8.

International Search Report dated Nov. 8, 2004, for International Application No. PCT/US2004/023880.

"Arena Pharmaceuticals Announces Preliminary Results of Phase 2b Clinical Trial of APD125 for the Treament of Insomnia", PRNewswire-FirstCall via COMTEX News Network, Press Release dated Dec. 9, 2008 (2 pp.).

Barluenga, J. et al., "A New and Specific Method for the Monomethylation of Primary Amines," J. Chem. Soc. Chem. Commun., 1984, 20, 1334-1335.

Batey, R.A. et al., "An Efficient New Protocol for the Formation of Unsymmetrical Tri-and Tetrasubstituted Ureas," Tetra. Lett., 1998, 39, 6267-6270.

Bernatowicz, M. et al., "A Comparison of Acid Labile Linkage Agents for the Synthesis of Peptide C-Terminal Amides," Tetra. Lett., 1989, 30(35), 4645-4648.

Burger, A., "Isosterism and bioisosterism in drug design", Prog. Drug Res., 37 (1991), pp. 287-371.

Gutsche, C.D. et al., "2-Phenylcycloheptanone," Org. Syn. Coll., 1963, vol. 4, 780-783.

Konig, W. et al., "A New Method for Synthesis of Peptides: Activation of the Carboxyl Group with Dicyclohexylcarbodiimide using 1-Hydroxybenzotriazoles as Additives," Chem. Ber., 1970, 103, 788-798 (English abstract included).

Marchini, P. et al., "Sodium Borohydride-Carboxylic Acid Systems. Useful Reagents for the Alkylation of Amines," J. Org. Chem., 1975, 40(23), 3453-3456.

Sahgal, A. (ed.), "Practical behavioral neuroscience: problems, pitfalls and suggestions," in Behavioral Neuroscience: A Practical Approach, IRL Press, New York, 1993, vol. 1, 1-8.

Sheehan, J.C. et al., "1-Ethyl-3-(3-Dimethylamiono)Propylcarbodiimide Hydrochloride and Methiodide," Org. Syn. Coll., 1973, vol. 5, 555-558.

Soresnon et al., "Characterization of the 5-HT.sub.2 Receptor Antagonist MDL 100907 as a Putative Atypical Antipsychotic: Behavioral, Electrophysical and Neurochemical Studies," J. Pharacol. Exp. Ther., 1993, 266(2), 684-691.

White, E., "Deamination of Amines. 2-Phenylethyl Benzoate Via the Nitrosoamide Decomposition," Org. Syn. Coll., 1973, vol. 5, 336-339.

International Search Report dated Nov. 8, 2004 for International Application No. PCT/US2004/023880.

International Search Report dated Dec. 10, 2004 for International Application No. PCT/US2004/023488.

International Search Report dated Feb. 20, 2007 for International Application No. PCT/US2006/002721.

Restriction Requirement dated May 12, 2009 for U.S. Appl. No. 11/833,043.

Affolter, H., "CA2+ as Messenger of 5HT2-Receptor Stimulation in Human Blood Platelets," Naunyn Schmiedebergs Arch. Pharmacol., 1984, vol. 325(4), 337-42.

Blier, P. et al., "Putative mechanisms of action of antidepressant drugs in affective and anxiety disorders and pain," Journal of Psychiatry and Neuroscience, 2000, vol. 26(1), 37-43.

Carter, H.E. et al., "Carbobenzoxy Chloride and Derivatives," Org. Syn. Coll., 1955, vol. 3, 167-169.

Catalán, J. et al., "New Ultraviolet Stabilizers: 3- and 5-(2'-Hydroxyphenyl)pyrazoles," J. Am. Chem. Soc., 114, 5039-5048 (1992).

Dosa, P.I. et al., "Synthesis and SAR of solubilized pyrazole derivatives as 5-HT2a inverse-agonists for platelet aggregration," 232th ACS National Meeting, Medi 431.

Elliot, J. M. et al., "4-Oxospiro[benzopyran-2,4'-piperidines] as Class III Antiarrhythmic Agents. Pharmacological Studies on 3,4-Dihydro-1'-[2-(benzofurazan-5-yl)-ethyl]-6methanesulfonamidospiro[(2H)-1-benzopyran-2,4'-piperidin]-4-one (L-691,121)", J. Med. Chem., 35:3973-3976 (1992).

Elphick, G. et al., "The human polyomavirus, JVC, uses serotonin to infect cells," Science, 2004, vol. 306, 1380-3.

Grotewiel et al., "Receptors Exhibit Constitutive Activity that is Blocked by Inverse Agonists," Faseb J., Abstract 353, 8(7), May 21-25, 1994.

Ieni, J. and Meyerson, L., "The 5-HT1A Receptor Probe [3H]8-OH-DPAT labels ...," Life Sciences, 1988, vol. 42, 311-320.

Ikeguchi, K. and Kuroda, A., "Mianserin Treatment of Patients with Pyschosis Induced by Antiparkinsonian Drugs," Eur. Arch. Psych. Clin. Neurosci., 1995, 244, 320-324.

Julius, D. et al., "The 5HT2 Receptor Defines a Family of Structurally Distinct but Functionally Conserved Serotonin Receptors," Proc. Natl. Acad. Sci. USA, 1990, vol. 87, 928-932.

Kanayama, M. et al,. "New treatment of lumbar disc herniation using 5-hydroxytryptamine2a receptor inhibitor: a randomized controlled trial," Journal of Neurosurgery: Spine, 2005, vol. 2, 441-6.

Kitagawa, O. et al., "Beckmann Rearrangement of O-4 Pentenyl Oxime through N-Bromosuccinimide-Mediated Activating Process", Chem. Pharm. Bull., 45(1) 32-35 (1997).

Mizuki, Y. et al., "Effects of Mianserin on Negative Symptoms in Schizophrenia," *Int. Clinical Psychopharmacology*, 1990, 5: 83-95.

Muto, T. et al., "Protective effects of sarpogrelate, a 5HT2A antagonist, against postischemic myocardial dysfunction in guinea-pig hearts," *Molecular and Cellular Biochemistry*, 2005, vol. 272, 119-32.

National Institutes of Health, "Facts about Insomnia," NIH Publication No. 95, 1995, 3801.

Newton, R.A. and Elliot, J.M., "Mianserin-Induced Down-Regulation of Human 5-Hydroxytryptamine2A and 5-Hydro . . . ," *Journal of Neurochemistry*, 1997, 69: 1031-1038.

Nishiyama, T., "Effects of 5HT2A receptor antagonist, sarpogrelate on thermal or inflammatory pain," *European Journal of Pharmacology*, 2005, vol. 516, 18-22.

Nomura, S. et al., "5HT2A receptor antagonist increases circulating adiponectin in patients with type 2 diabetes," *Blood Coagulation and Fibrinolysis*, 2005, vol. 16(6), 423-8.

Sawnyok, J. et al., "Antidepressants as analgesics: an overview of central and peripheral mechanisms of action," *Journal of Psychiatry and Neurosciences*, 2001, vol. 26(1), 21-9.

Schmidt, C., "The Role of 5-HT2A Receptors in Antipsychotic Activity," *Life Sciences*, 1995, 56(25), 2209-2222.

Shibata, R. et al., "Adiponectin protects against myocardial ischemiareperfusion injury through AMPK- and COX-2 dependent mechanisms," *Nature Medicine*, advanced online Publications: 1-8.

Van Zwieten, PA, "Receptors Involved in the Regulation of Vascular Tone," *Arzneimittelforschung*. 1985, vol. 35(12A): 1904-9.

Verstraete, M., "Prevention of atherosclerotic complications: controlled trial of ketanserin," *British Medical Journal*, 1989, vol. 298, 424-30.

Vikenes, K. et al., "Serotonin is associated with coronary artery disease and cardiac events," *Circulation*, 1999, vol. 100, 483-9.

Vippagunta, S. et al., "Crystalline solids," *Advanced Drug Delivery Reviews*, 48:3-26 (2001).

Wikstrom, H. et al., "Synthesis and Pharmacological Testing of 1, 2, 3, 4, 10, 14b-Hexahydro-6-methoxy . . . ," *J. Med. Chem.*, 2002, vol. 45, 3280-3285.

International Search Report for International Applicaion No. PCT/US2005/041726 dated May 18, 2006 by Authorized Officer Stefan Härtinger.

International Search Report for International Application No. PCT/US2006/001516 dated Jun. 7, 2006.

International Preliminary Report on Patentability for International Application No. PCT/US2005/041726 dated Sep. 21, 2006 by Authorized Officer Stefan Härtinger.

Written Opinion of the International Searching Authority for International Application No. PCT/US2005/041726.

International Search Report for International Application No. PCT/US2007/011810 dated Oct. 30, 2007 by Authorized Officer Bart De Jong.

International Preliminary Report on Patentability for International Application No. PCT/US2007/011810 dated Jul. 16, 2008 by Authorized Officer Bart De Jong.

Nichols, et al. J. Med Chem, 1991, 34, 276-81. See page 302.

Tang, et al., Bioorg. Med. Chem. Lett. 203, 13, 2985-88. See Table 1 and p. 2987.

Yevich et al. Curr. Med.Chem., 1997, 4(5), 295-312. See p. 302.

Chambers, et al., Bioorg., Med. Chem. Lett. 2002, 12 1997-99. See page 1997-98.

Glennon, et al., J. Med. Chem., 1982, 25(10), 1163-68. See p. 1166-67 and Table II.

Holtje, the Practice of Medicinal Chemistry, 2$^{nd}$ ed., 2003, Wermuth (editor), Academic Press, pp. 387-403. See p. 394.

"QuaSAR" Research Monograph 22, 1978, NIDA, Barnett and Willette (eds.) See pp. 16-25 pp. 159-179, Tables 1-8.

John Mandel, "Statistical Analysis of Experimental Data", Chapter 3, pp. 28-57, Toronto, Ontario, (1964).

John Mandel, "Statistical Analysis of Experimental Data", Chapter 9, pp. 204-207, Toronto, Ontario, (1964).

Westkaemper et al., Curr. Topics Med. Chem., 2002, 2, 575-598.

Office Action for U.S. Appl. No. 11/883,043, mailed on Sep. 8, 2009.

PROCESSES FOR PREPARING SUBSTITUTED N-ARYL-N'-[3-(1H-PYRAZOL-5-YL) PHENYL] UREAS AND INTERMEDIATES THEREOF

CROSS REFERENCE TO RELATED APPLICATIONS

This application is a 35 U.S.C. §371 National Stage Application of International Application No. PCT/US2004/023880, filed Jul. 21, 2004, which claims priority to U.S. Ser. No. 60/555,626, filed Mar. 23, 2004.

FIELD OF THE INVENTION

The present invention is directed to processes for the preparation of substituted phenylpyrazole ureas that are useful as 5-HT$_{2A}$ serotonin receptor modulators for the treatment of disease.

BACKGROUND OF THE INVENTION

G protein-coupled receptors share a common structural motif. All these receptors have seven sequences of between 22 to 24 hydrophobic amino acids that form seven alpha helices, each of which spans the membrane. The transmembrane helices are joined by strands of amino acids having a larger loop between the fourth and fifth transmembrane helix on the extracellular side of the membrane. Another larger loop, composed primarily of hydrophilic amino acids, joins transmembrane helices five and six on the intracellular side of the membrane. The carboxy terminus of the receptor lies intracellularly with the amino terminus in the extracellular space. It is thought that the loop joining helices five and six, as well as, the carboxy terminus, interact with the G protein. Currently, Gq, Gs, Gi and Go are G proteins that have been identified.

Under physiological conditions, G protein-coupled receptors exist in the cell membrane in equilibrium between two different states or conformations: an "inactive" state and an "active" state. A receptor in an inactive state is unable to link to the intracellular transduction pathway to produce a biological response. Changing the receptor conformation to the active state allows linkage to the transduction pathway and produces a biological response.

A receptor may be stabilized in an active state by an endogenous ligand or an exogenous agonist ligand. Recent discoveries such as, including but not exclusively limited to, modifications to the amino acid sequence of the receptor provide means other than ligands to stabilize the active state conformation. These means effectively stabilize the receptor in an active state by simulating the effect of a ligand binding to the receptor. Stabilization by such ligand-independent means is termed "constitutive receptor activation."

Receptors for serotonin (5-hydroxytryptamine, 5-HT) are an important class of G protein-coupled receptors. Serotonin is thought to play a role in processes related to learning and memory, sleep, thermoregulation, mood, motor activity, pain, sexual and aggressive behaviors, appetite, neurodegenerative regulation, and biological rhythms. Not surprisingly, serotonin is linked to pathophysiological conditions such as anxiety, depression, obsessive-compulsive disorders, schizophrenia, suicide, autism, migraine, emesis, alcoholism, and neurodegenerative disorders. With respect to an anti-psychotic treatment, approaches focused on the serotonin receptors, these types of therapeutics can generally be divided into two classes, the "typical" and the "atypical." Both have anti-psychotic effects, but the typicals also include concomitant motor-related side effects (extra pyramidal syndromes, e.g., lip-smacking, tongue darting, locomotor movement, etc). Such side effects are thought to be associated with the compounds interacting with other receptors, such as the human dopamine D2 receptor in the nigro-striatal pathway. Therefore, an atypical treatment is preferred. Haloperidol is considered a typical anti-psychotic, and clozapine is considered an atypical anti-psychotic.

Serotonin receptors are divided into seven subfamilies, referred to as 5-HT$_1$ through 5-HT$_7$, inclusive. These subfamilies are further divided into subtypes. For example, the 5-HT$_2$ subfamily is divided into three receptor subtypes: 5-HT$_{2A}$, 5-HT$_{2B}$, and 5-HT$_{2C}$. The human 5-HT$_{2C}$ receptor was first isolated and cloned in 1987, and the human 5-HT$_{2A}$ receptor was first isolated and cloned in 1990. These two receptors are thought to be the site of action of hallucinogenic drugs. Additionally, antagonists to the 5-HT$_{2A}$ and 5-HT$_{2C}$ receptors are believed to be useful in treating depression, anxiety, psychosis, and eating disorders.

Isolation, characterization, and expression of a functional cDNA clone encoding the entire human 5-HT$_{1C}$ receptor (now known as the 5-HT$_{2C}$ receptor) and the entire human 5-HT$_{2A}$ receptor are described in U.S. Pat. Nos. 4,985,352 and 5,661,012, respectively. Mutations of the endogenous forms of the rat 5-HT$_{2A}$ and rat 5-HT$_{2C}$ receptors have been reported to lead to constitutive activation of these receptors (5-HT$_{2A}$: Casey, C. et al. (1996) *Society for Neuroscience Abstracts*, 22:699.10, 5-HT$_{2C}$: Herrick-Davis, K., and Teitler, M. (1996) *Society for Neuroscience Abstracts*, 22:699.18; and Herrick-Davis, K. et al. (1997) *J. Neurochemistry* 69(3): 1138).

Small molecule modulators of serotonin receptors have been shown to have a variety of therapeutic applications such as for the treatment of any of the diseases listed above. Accordingly, there is an ongoing need for the preparation of compounds that can modulate serotonin receptors. The processes and intermediates described are directed to this and other needs.

SUMMARY OF THE INVENTION

The present invention provides processes for preparing compounds of Formula (I):

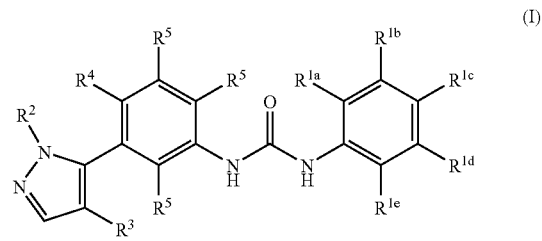

wherein constituent members are defined herein; comprising:
a) reacting a compound of Formula (II):

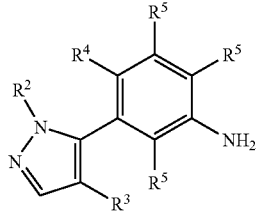
(II)

with a compound of Formula (III):

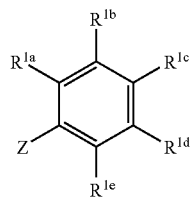
(III)

wherein Z is an isocyanate group (—NCO) or isocyanate equivalent, for a time and under conditions suitable for forming said compound of Formula (I); or
b) reacting a compound of Formula (II) with an isocyanate-generating reagent for a time and under conditions suitable for forming a compound of Formula (IIa):

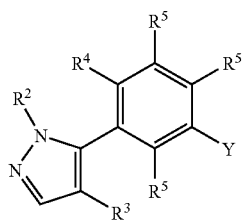
(IIa)

wherein Y is an isocyanate group or isocyanate equivalent; and reacting said compound of Formula (IIa) with a compound of Formula (IIIa):

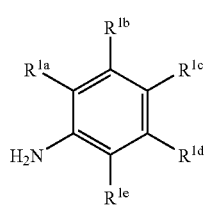
(IIIa)

for a time and under conditions suitable for forming said compound of Formula (I).

The present invention further provides processes for preparing compounds of Formula (II) comprising reacting a compound of Formula (IV):

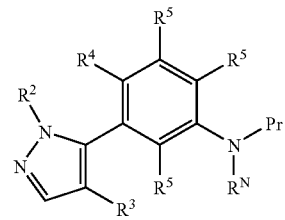
(IV)

wherein:
Pr is an amino protecting group; and
$R^N$ is H;
or Pr and $R^N$ together with the N atom to which they are attached form a cyclic amino protecting group; with a deprotecting agent for a time and under conditions suitable for forming said compound of Formula (II).

The invention further provides processes for preparing compounds of Formula (IV) comprising reacting a compound of Formula (V):

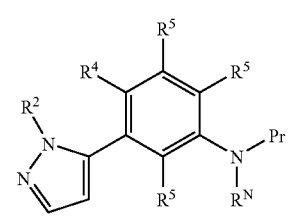
(V)

with a halogenating reagent for a time and under conditions suitable for forming said compound of Formula (IV).

The present invention further provides processes for preparing compounds of Formula (V) comprising reacting a compound of Formula (VI):

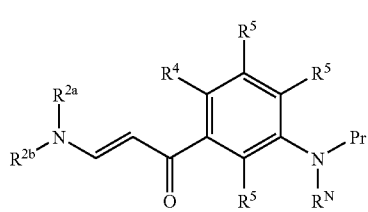
(VI)

wherein $R^{2a}$ and $R^{2b}$ are each, independently, $C_{1-4}$ alkyl; with an alkylhydrazine having the formula $NH_2NH—R^2$ for a time and under conditions suitable for forming said compound of Formula (V).

The present invention further provides processes for preparing compounds of Formula (VI) comprising reacting a compound of Formula (VII):

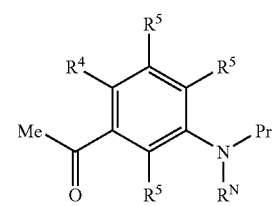
(VII)

with an acetal of Formula (VIII):

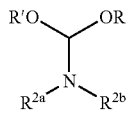

(VIII)

wherein R and R' are each, independently, $C_{1-6}$ alkyl, arylalkyl or alkylaryl, or R and R' together with the O atoms to which they are attached and the intervening CH group form a 5- or 6-membered heterocycloalkyl group, for a time and under conditions suitable for forming said compound of Formula (VI).

The present invention further provides process intermediates for Formulae (II), (IV), (V) and (VI):

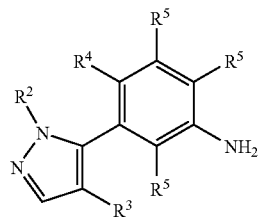

(II)

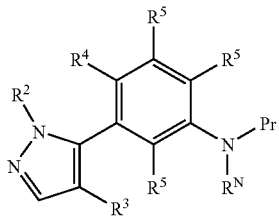

(IV)

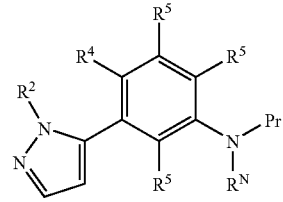

(V)

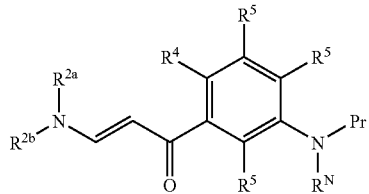

(VI)

wherein constituent members are provided herein.

DETAILED DESCRIPTION

The present invention is directed to processes and intermediates for the preparation of substituted phenylpyrazole ureas that are useful as 5-$HT_{2A}$ serotonin receptor modulators for the treatment of disorders mediated by 5-$HT_{2A}$ serotonin receptor expression and/or activity such as, for example, central nervous system disorders (e.g., dementia, behavioral disorders, psychoses, Gilles de la Tourette's syndrome, manic disorder, schizophrenia, and the like), cardiovascular disorders (e.g., coronary artery disease, myocardial infarction, transient ischemic attack, angina, stroke, atrial fibrillation, and the like), sleep disorders, and other disorders.

Example processes and intermediates of the present invention are provided below in Schemes Ia and Ib, wherein constituent members of the compounds depicted therein are defined below.

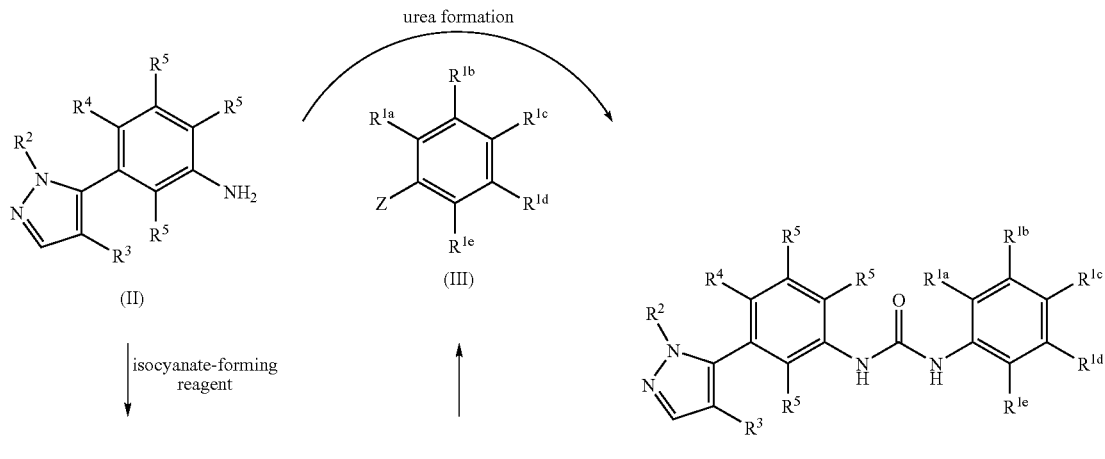

Scheme Ia

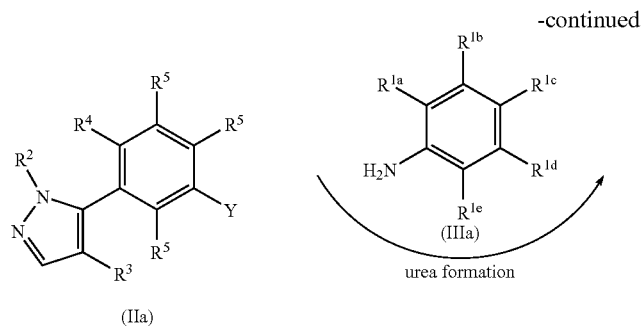

(IIa)     (IIIa) urea formation

Scheme Ib

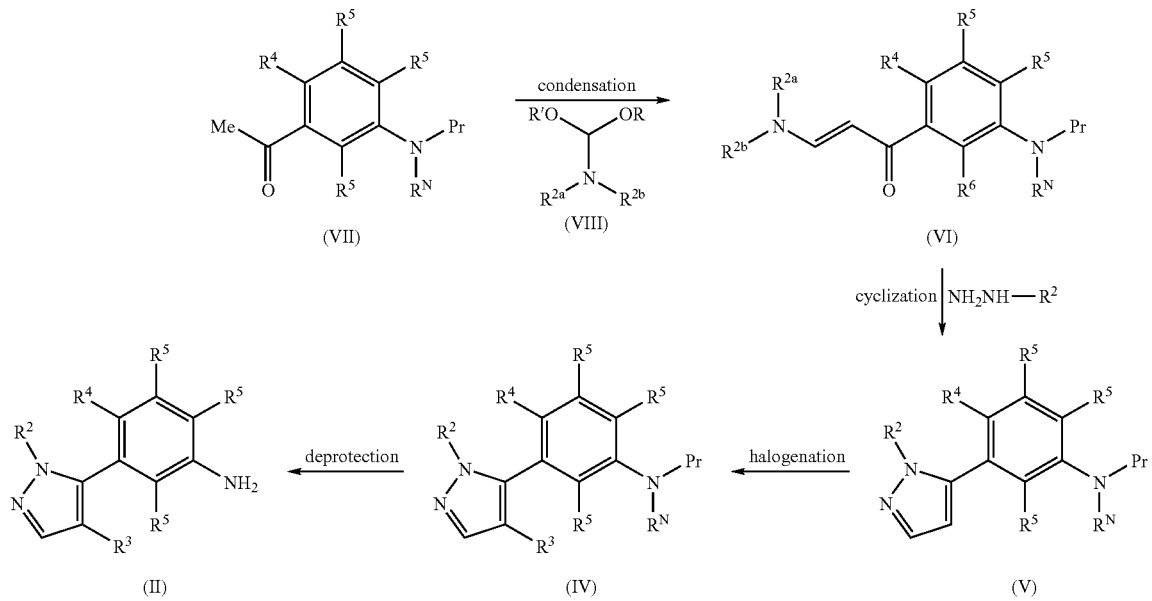

In a first aspect of the invention are provided processes, such as are exemplified by Schemes Ia and Ib (supra) and Ic and Id (infra), that involve compounds of Formulas (I), (II), (IIa), (IIc), (IId), (III), (IIIa), (IV), (IVa), (V), (Vb), (VI), (VIa), (VII), (VIIa) and (VIII), or salt forms thereof, wherein:

$R^{1a}$, $R^{1b}$, $R^{1c}$, $R^{1d}$, and $R^{1e}$ are each, independently, H, halo, cyano, nitro, $C_{1-6}$ alkyl, $C_{1-6}$ haloalkyl, $C_{2-6}$ alkenyl, $C_{2-6}$ alkynyl, $OR^7$, $SR^7$, $SOR^8$, $SO_2R^8$, $COR^8$, $COOR^7$, $OC(O)R^8$, $NR^9R^{10}$, carbocyclyl optionally substituted by one or more $R^6$ or heterocyclyl optionally substituted by one or more $R^6$; or $R^{1a}$ and $R^{1b}$, $R^{1b}$ and $R^{1c}$, $R^{1c}$ and $R^{1d}$, or $R^{1d}$ and $R^{1e}$ together with the carbon atoms to which they are attached form a fused $C_{5-7}$ cycloalkyl group or fused $C_{5-7}$ heterocycloalkyl group; wherein each of said $C_{1-6}$ alkyl, $C_{2-6}$ alkenyl, and $C_{2-6}$ alkynyl, is optionally substituted with one or more $C_{1-6}$ acyl, $C_{1-6}$ acyloxy, $C_{1-6}$ alkoxy, $C_{1-6}$ thioalkoxy, carboxamide, $C_{1-6}$ alkylcarboxamide, $C_{2-8}$ dialkylcarboxamide, $C_{1-6}$ alkylsulfonamide, $C_{1-6}$ alkylsulfinyl, $C_{1-6}$ alkylsulfonyl, $C_{1-6}$ alkylureido, amino, $C_{1-6}$ alkylamino, $C_{2-8}$ dialkylamino, $C_{1-6}$ alkoxycarbonyl, carboxy, cyano, $C_{3-7}$ cycloalkyl, halogen, $C_{1-6}$ haloalkoxy, $C_{1-6}$ halothioalkoxy, $C_{1-6}$ haloalkyl, $C_{1-6}$ haloalkylsulfinyl, $C_{1-6}$ haloalkylsulfonyl, hydroxyl, mercapto or nitro;

$R^2$ is $C_{1-4}$ alkyl;

$R^3$ is F, Cl, Br or I;

$R^4$ is halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, $SR^{11}$, $SOR^{12}$, $SO_2R^{12}$, $COR^{12}$, $COOR^{11}$, $OC(O)R^{12}$, $NR^{13}R^{14}$, or $C_{3-7}$ cycloalkyl, wherein said $C_{1-6}$ alkoxy group is optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms;

$R^5$, at each independent occurrence, is H, halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, $SR^{11}$, $SOR^{12}$, $SO_2R^{12}$, $COR^{12}$, $COOR^{11}$, $OC(O)R^{12}$, $NR^{13}R^{14}$, or $C_{3-7}$ cycloalkyl, wherein said $C_{1-6}$ alkoxy group is optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms;

$R^6$ is halo, cyano, nitro, $C_{1-4}$ alkyl, $C_{1-4}$ haloalkyl, $C_{1-4}$ alkoxy, $C_{1-4}$ haloalkoxy, amino, ($C_{1-4}$ alkyl)amino, di($C_{1-4}$ alkyl)amino, hydroxy, carboxy, ($C_{1-4}$ alkoxy)carbonyl, $C_{1-4}$ acyl, $C_{1-4}$ acyloxy, aminocarbonyl, ($C_{1-4}$ alkyl)aminocarbonyl, or di($C_{1-4}$ alkyl)aminocarbonyl;

$R^7$ and $R^{11}$ are each, independently, H, $C_{1-8}$ alkyl, $C_{1-8}$ haloalkyl, $C_{2-8}$ alkenyl, $C_{2-8}$ alkynyl, aryl, heteroaryl, $C_{3-7}$ cycloalkyl, 5-7 membered heterocycloalkyl, arylalkyl, heteroarylalkyl, ($C_{3-7}$ cycloalkyl)alkyl or (5-7 membered heterocycloalkyl)alkyl;

$R^8$ and $R^{12}$ are each, independently, H, $C_{1-8}$ alkyl, $C_{1-8}$ haloalkyl, $C_{2-8}$ alkenyl, $C_{2-8}$ alkynyl, aryl, heteroaryl, $C_{3-7}$ cycloalkyl, 5-7 membered heterocycloalkyl, arylalkyl, heteroarylalkyl, ($C_{3-7}$ cycloalkyl)alkyl, (5-7 membered heterocycloalkyl)alkyl, amino, ($C_{1-4}$ alkyl)amino, or di($C_{1-4}$ alkyl)amino;

$R^9$ and $R^{10}$ are each, independently, H, $C_{1-8}$ alkyl, $C_{2-8}$ alkenyl, $C_{2-8}$ alkynyl, aryl, heteroaryl, $C_{3-7}$ cycloalkyl, 5-7 membered heterocycloalkyl, arylalkyl, heteroarylalkyl, ($C_{3-7}$ cycloalkyl)alkyl, (5-7 membered heterocycloalkyl)alkyl, ($C_{1-8}$ alkyl)carbonyl, ($C_{1-8}$ haloalkyl)carbonyl, ($C_{1-8}$ alkoxy)carbonyl, ($C_{1-8}$ haloalkoxy)carbonyl, ($C_{1-4}$ alkyl)sulfonyl, ($C_{1-4}$ haloalkyl)sulfonyl or arylsulfonyl;

or $R^9$ and $R^{10}$, together with the N atom to which they are attached form a 5-7 membered heterocycloalkyl group;

$R^{13}$ and $R^{14}$ are each, independently, H, $C_{1-8}$ alkyl, $C_{2-8}$ alkenyl, $C_{2-8}$ alkynyl, aryl, heteroaryl, $C_{3-7}$ cycloalkyl, 5-7 membered heterocycloalkyl, arylalkyl, heteroarylalkyl, ($C_{3-7}$ cycloalkyl)alkyl, (5-7 membered heterocycloalkyl)alkyl, ($C_{1-8}$ alkyl)carbonyl, ($C_{1-8}$ haloalkyl)carbonyl, ($C_{1-8}$ alkoxy)carbonyl, ($C_{1-8}$ haloalkoxy)carbonyl, ($C_{1-4}$ alkyl)sulfonyl, ($C_{1-4}$ haloalkyl)sulfonyl or arylsulfonyl;

or $R^{13}$ and $R^{14}$, together with the N atom to which they are attached form a 5-7 membered heterocycloalkyl group;

Pr is an amino protecting group;

$R^N$ is H;

or Pr and $R^N$ together with the N atom to which they are attached form a cyclic amino protecting group;

$R^{2a}$ and $R^{2b}$ are each, independently, $C_{1-4}$ alkyl;

R and R' are each, independently, $C_{1-6}$ alkyl, arylalkyl or alkylaryl, or R and R' together with the O atoms to which they are attached and the intervening CH group form a 5- or 6-membered heterocycloalkyl group;

Y is an isocyanate group (—NCO) or isocyanate equivalent; and

Z is an isocyanate group (—NCO) or isocyanate equivalent.

In some embodiments, $R^{1a}$, $R^{1b}$, $R^{1c}$, $R^{1d}$, and $R^{1e}$ are each, independently, H, halo, cyano, nitro, $C_{1-6}$ alkyl, $C_{1-6}$ haloalkyl, $C_{2-6}$ alkenyl, $C_{2-6}$ alkynyl, $OR^7$, $SR^7$, $SOR^8$, $SO_2R^8$, $COR^8$, $COOR^7$, $OC(O)R^8$, $NR^9R^{10}$, carbocyclyl optionally substituted by one or more $R^6$ or heterocyclyl optionally substituted by one or more $R^6$.

It is understood that when more than one $R^6$ is present they may be the same group or a different group.

In some embodiments, $R^{1a}$, $R^{1b}$, $R^{1c}$, $R^{1d}$, and $R^{1e}$ are each, independently, H, halo, cyano, nitro, $C_{1-6}$ alkyl, $C_{1-6}$ haloalkyl, $C_{2-6}$ alkenyl, $C_{2-6}$ alkynyl, $OR^7$ or carbocyclyl optionally substituted by one or more $R^6$.

In some embodiments, $R^{1a}$, $R^{1b}$, $R^{1c}$, $R^{1d}$, and $R^{1e}$ each, independently, H, halo, $C_{1-6}$ alkyl, $C_{1-6}$ haloalkyl, $C_{1-6}$ alkyl, or $C_{1-6}$ haloalkyl.

In some embodiments, $R^{1a}$, $R^{1b}$, $R^{1c}$, $R^{1d}$, and $R^{1e}$ are each, independently, H, F, Cl, Br, or I.

In some embodiments, $R^{1a}$ is H or halo, $R^{1b}$ is H, $R^{1c}$ is halo, $R^{1d}$ is H, and $R^{1e}$ is H.

In some embodiments, $R^{1a}$ is halo, $R^{1b}$ is H, $R^{1c}$ is halo, $R^{1d}$ is H, and $R^{1e}$ is H.

In some embodiments:
$R^{1a}$ is F, $R^{1b}$ is H, $R^{1c}$ is F, $R^{1d}$ is H, and $R^{1e}$ is H;
$R^{1a}$ is H, $R^{1b}$ is H, $R^{1c}$ is Cl, $R^{1d}$ is H, and $R^{1e}$ is H;
$R^{1a}$ is H, $R^{1b}$ is H, $R^{1c}$ is F, $R^{1d}$ is H, and $R^{1e}$ is H; or
$R^{1a}$ is H, $R^{1b}$ is H, $R^{1c}$ is Cl, $R^{1d}$ is H, and $R^{1e}$ is H.

In some embodiments, $R^2$ is methyl or ethyl.
In some embodiments, $R^2$ is methyl.
In some embodiments, $R^3$ is Cl or Br.
In some embodiments, $R^3$ is Br.

In some embodiments, $R^4$ is halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, wherein said $C_{1-6}$ alkoxy group is optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms.

In some embodiments, $R^4$ is $C_{1-6}$ alkoxy optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms.

In some embodiments, $R^4$ is $C_{1-6}$ alkoxy.
In some embodiments, $R^4$ is $C_{1-3}$ alkoxy.
In some embodiments, $R^4$ is methoxy or ethoxy.
In some embodiments, $R^4$ is methoxy.

In some embodiments, $R^5$, at each independent occurrence, is H, halo, cyano, nitro, $C_{1-6}$ alkyl, $C_{1-6}$ haloalkyl, $C_{2-6}$ alkenyl, $C_{2-6}$ alkynyl, or $C_{1-6}$ alkoxy.

In some embodiments, $R^5$, at each independent occurrence, is H or halo.

In some embodiments, $R^5$, at each occurrence, is H.
In some embodiments, R and R' are both $C_{1-4}$ alkyl.
In some embodiments, R and R' are both methyl.
In some embodiments, $R^{2a}$ and $R^{2b}$ are both methyl.
In some embodiments, Pr is an acyl group.
In some embodiments, Pr is —C(O)—($C_{1-4}$ alkyl).
In some embodiments, Pr is —C(O)Me.
In some embodiments:
$R^{1a}$, $R^{1b}$, $R^{1c}$, $R^{1d}$, and $R^{1e}$ are each, independently, H, halo, cyano, nitro, $C_{1-6}$ alkyl, $C_{1-6}$ haloalkyl, $C_{2-6}$ alkenyl, $C_{2-6}$ alkynyl, $OR^7$, $SR^7$, $SOR^8$, $SO_2R^8$, $COR^8$, $COOR^7$, $OC(O)R^8$, $NR^9R^{10}$, carbocyclyl optionally substituted by one or more $R^6$ or heterocyclyl optionally substituted by one or more $R^6$;

$R^3$ is F, Cl, Br or I;

$R^4$ is halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, wherein said $C_{1-6}$ alkoxy group is optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms; and $R^5$, at each independent occurrence, is H, halo, cyano, nitro, $C_{1-6}$ alkyl, $C_{1-6}$ haloalkyl, $C_{2-6}$ alkenyl, $C_{2-6}$ alkynyl, or $C_{1-6}$ alkoxy.

In some embodiments:

$R^{1a}$, $R^{1b}$, $R^{1c}$, $R^{1d}$, and $R^{1e}$ are each, independently, H, halo, $C_{1-6}$ alkyl, $C_{1-6}$ haloalkyl, $C_{1-6}$ alkyl, or $C_{1-6}$ haloalkyl;

$R^3$ is F, Cl, Br or I;

$R^4$ is $C_{1-6}$ alkoxy group optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms; and $R^5$, at each occurrence, is H.

In some embodiments:

$R^{1a}$, $R^{1b}$, $R^{1c}$, $R^{1d}$, and $R^{1e}$ are each, independently, H, F, Cl, Br or I;

$R^2$ is methyl or ethyl;

$R^3$ is F, Cl, Br or I;

$R^4$ is $C_{1-6}$ alkoxy; and $R^5$, at each occurrence, is H.

In some embodiments:

$R^{1a}$, $R^{1b}$, $R^{1c}$, $R^{1d}$, and $R^{1e}$ are each, independently, H, F, or Cl;

$R^2$ is methyl;

$R^3$ is Cl or Br;

$R^4$ is methoxy; and $R^5$, at each occurrence, is H.

In some embodiments:

$R^{1a}$ is F;

$R^{1b}$ is H;

$R^{1c}$ is F;

$R^{1d}$ is H;

$R^{1e}$ is H;

$R^2$ is methyl;

$R^3$ is Br;

$R^4$ is methoxy; and $R^5$, at each occurrence, is H.

In some embodiments:

$R^{1a}$ is H;

$R^{1b}$ is H;

$R^{1c}$ is Cl;

$R^{1d}$ is H;

$R^{1e}$ is H;

$R^2$ is methyl;

$R^3$ is Br;

$R^4$ is methoxy; and $R^5$, at each occurrence, is H.

In some embodiments:

$R^{1a}$ is H;

$R^{1b}$ is H;

$R^{1c}$ is F;

$R^{1d}$ is H;

$R^{1e}$ is H;

$R^2$ is methyl;

$R^3$ is Br;

$R^4$ is methoxy; and $R^5$, at each occurrence, is H.

In some embodiments:

$R^{1a}$ is H;

$R^{1b}$ is H;

$R^{1c}$ is Cl;

$R^{1d}$ is H;

$R^{1e}$ is H;

$R^2$ is methyl;

$R^3$ is Cl;

$R^4$ is methoxy; and $R^5$, at each occurrence, is H.

In some embodiments, Z is —NCO.

In some embodiments, Y is —NCO.

In some embodiments:

$R^3$ is F, Cl, Br or I;

$R^4$ is halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, wherein said $C_{1-6}$ alkoxy group is optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonanide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms; and $R^5$ is H, halo, cyano, nitro, $C_{1-6}$ alkyl, $C_{1-6}$ haloalkyl, $C_{2-6}$ alkenyl, $C_{2-6}$ alkynyl, or $C_{1-6}$ alkoxy.

In some embodiments:

$R^3$ is F, Cl, Br or I;

$R^4$ is $C_{1-6}$ alkoxy group optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms; and $R^5$, at each occurrence, is H.

In some embodiments:

$R^2$ is methyl or ethyl;

$R^3$ is F, Cl, Br or I;

$R^4$ is $C_{1-6}$ alkoxy; and $R^5$, at each occurrence, is H.

In some embodiments:

$R^2$ is methyl;

$R^3$ is Cl or Br;

$R^4$ is methoxy; and $R^5$, at each occurrence, is H.

In some embodiments, for compounds of Formula (II), $R^2$ is methyl; $R^3$ is Cl or Br; $R^4$ is methoxy; and $R^5$, at each occurrence, is H.

In some embodiments, for compounds of Formula (II), $R^2$ is methyl; $R^3$ is Br; $R^4$ is methoxy; and $R^5$, at each occurrence, is H.

In some embodiments, for compounds of Formula (II), $R^2$ is methyl; $R^3$ is Cl; $R^4$ is methoxy; and $R^5$, at each occurrence, is H.

In some embodiments, for compounds of Formula (IV), $R^2$ is methyl; $R^3$ is Br; $R^4$ is methoxy; $R^5$, at each occurrence, is H; and Pr is —C(O)Me.

In some embodiments, for compounds of Formula (IV), $R^2$ is methyl; $R^3$ is Cl; $R^4$ is methoxy; $R^5$, at each occurrence, is H; and Pr is —C(O)Me.

In some embodiments, for compounds of Formula (V), $R^2$ is methyl; $R^4$ is methoxy; $R^5$, at each occurrence, is H; and Pr is —C(O)Me.

In some embodiments, for compounds of Formula (VI), $R^{2a}$ is methyl; $R^{2b}$ is methyl; $R^4$ is methoxy; $R^5$, at each occurrence, is H; and Pr is —C(O)Me.

$R^{1e}$ is H;

$R^2$ is methyl;

$R^3$ is Cl;

$R^4$ is methoxy; and $R^5$, at each occurrence, is H.

Further example processes and intermediates of the present invention are provided below in Schemes Ic and Id, wherein constituent members of the compounds depicted therein are defined in this disclosure, supra and infra.
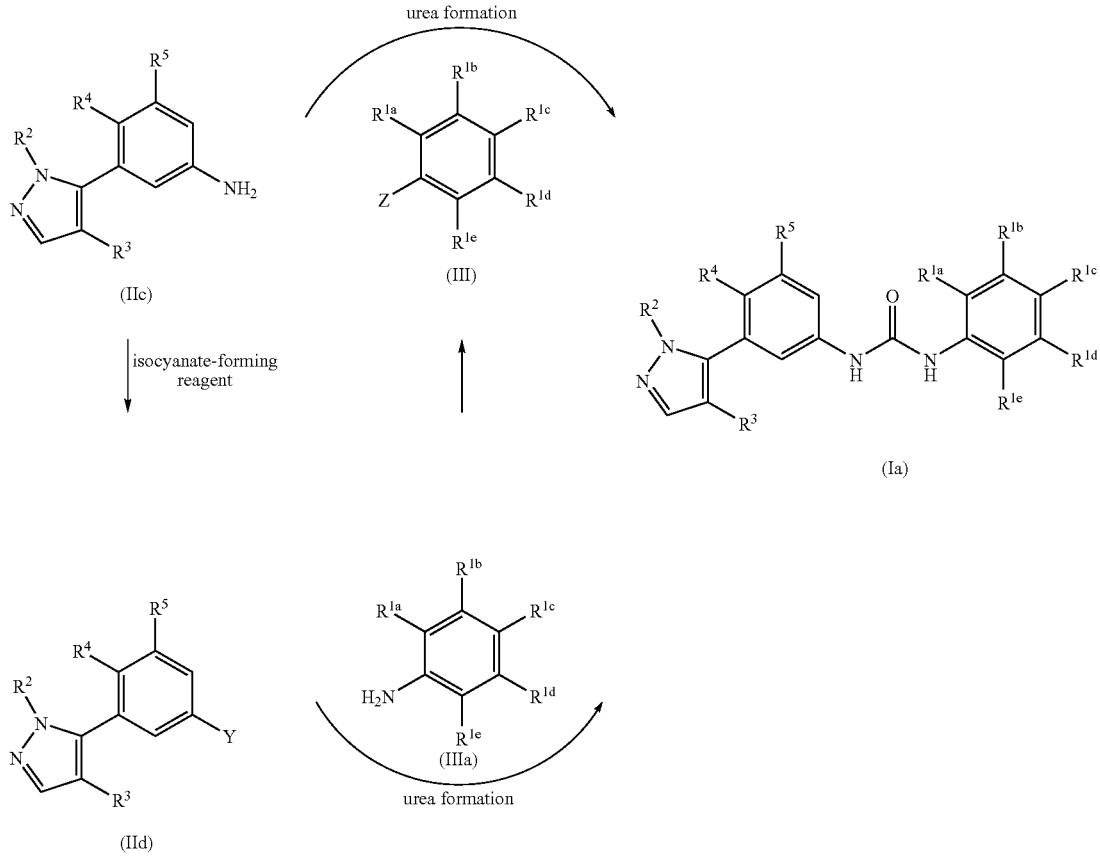
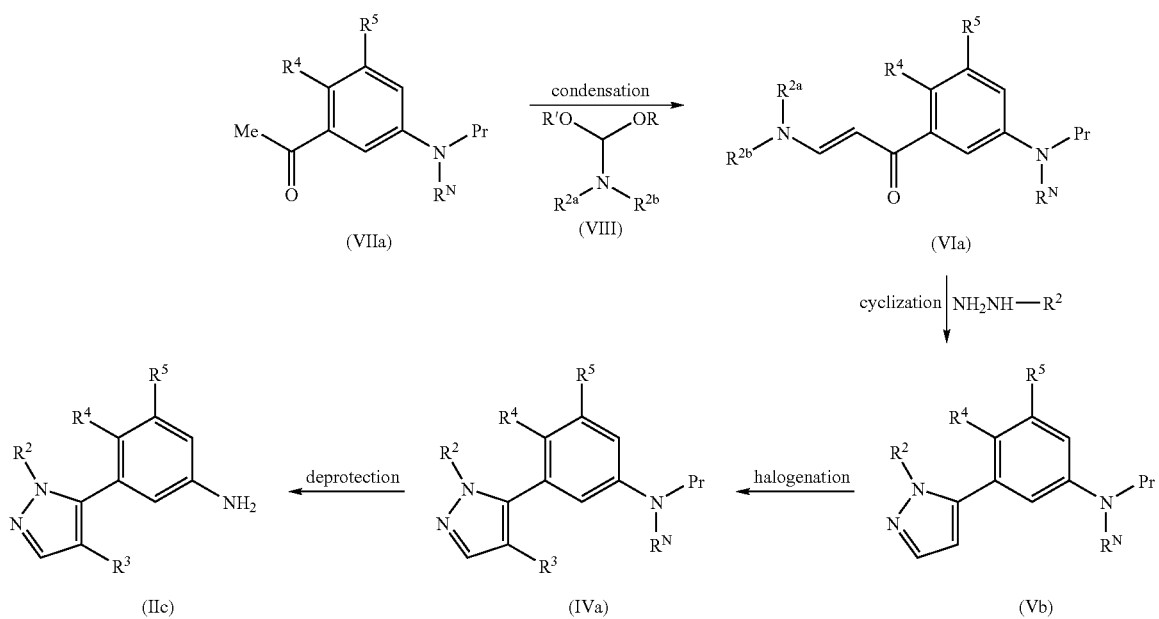

Some embodiments of the present invention provide processes, such as are exemplified by Scheme Ic and Id, that involve compounds of Formulae (Ia), (IIc), (IId), (III), (IIIa), (IVa), (Vb), (VIa), (VIIa) and (VIII), or salt forms thereof, wherein:

$R^{1a}$, $R^{1b}$, $R^{1c}$, $R^{1d}$, and $R^{1e}$ are each, independently, H, halo, cyano, nitro, $C_{1-6}$ alkyl, $C_{1-6}$ haloalkyl, $C_{2-6}$ alkenyl, $C_{2-6}$ alkynyl, $OR^7$, $SR^7$, $SOR^8$, $SO_2R^8$, $COR^8$, $COOR^7$, $OC(O)R^8$, $NR^9R^{10}$, carbocyclyl optionally substituted by one or more $R^6$ or heterocyclyl optionally substituted by one or more $R^6$; or $R^{1a}$ and $R^{1b}$, $R^{1b}$ and $R^{1c}$, $R^{1c}$ and $R^{1d}$, or $R^{1d}$ and $R^{1e}$ together with the carbon atoms to which they are attached form a fused $C_{5-7}$ cycloalkyl group or fused $C_{5-7}$ heterocycloalkyl group; wherein each of said $C_{1-6}$ alkyl, $C_{2-6}$ alkenyl, and $C_{2-6}$ alkynyl, is optionally substituted with one or more $C_{1-6}$ acyl, $C_{1-6}$ acyloxy, $C_{1-6}$ alkoxy, $C_{1-6}$ thioalkoxy, carboxamide, $C_{1-6}$ alkylcarboxamide, $C_{2-8}$ dialkylcarboxamide, $C_{1-6}$ alkylsulfonamide, $C_{1-6}$ alkylsulfinyl, $C_{1-6}$ alkylsulfonyl, $C_{1-6}$ alkylureido, amino, $C_{1-6}$ alkylamino, $C_{2-8}$ dialkylamino, $C_{1-6}$ alkoxycarbonyl, carboxy, cyano, $C_{3-7}$ cycloalkyl, halogen, $C_{1-6}$ haloalkoxy, $C_{1-6}$ halothioalkoxy, $C_{1-6}$ haloalkyl, $C_{1-6}$ haloalkylsulfinyl, $C_{1-6}$ haloalkylsulfonyl, hydroxyl, mercapto or nitro;

$R^2$ is $C_{1-4}$ alkyl;

$R^3$ is F, Cl, Br or I;

$R^4$ is halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, $SR^{11}$, $SOR^{12}$, $SO_2R^{12}$, $COR^{12}$, $COOR^{11}$, $OC(O)R^{12}$, $NR^{13}R^{14}$, or $C_{3-7}$ cycloalkyl, wherein said $C_{1-6}$ alkoxy group is optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms;

$R^5$ is H, halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, $SR^{11}$, $SOR^{12}$, $SO_2R^{12}$, $COR^{12}$, $COOR^{11}$, $OC(O)R^{12}$, $NR^{13}R^{14}$, or $C_{3-7}$ cycloalkyl, wherein said $C_{1-6}$ alkoxy group is optionally substituted with one or more $C_{1-5}$ acyl, $C_{1-5}$ acyloxy, $C_{2-6}$ alkenyl, $C_{14}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms;

$R^6$ is halo, cyano, nitro, $C_{1-4}$ alkyl, $C_{1-4}$ haloalkyl, $C_{1-4}$ alkoxy, $C_{1-4}$ haloalkoxy, amino, ($C_{1-4}$ alkyl)amino, di($C_{1-4}$ alkyl)amino, hydroxy, carboxy, ($C_{1-4}$ alkoxy)carbonyl, $C_{1-4}$ acyl, $C_{1-4}$ acyloxy, aminocarbonyl, ($C_{1-4}$ alkyl)aminocarbonyl, or di($C_{1-4}$ alkyl)aminocarbonyl;

$R^7$ and $R^{11}$ are each, independently, H, $C_{1-8}$ alkyl, $C_{1-8}$ haloalkyl, $C_{2-8}$ alkenyl, $C_{2-8}$ alkynyl, aryl, heteroaryl, $C_{3-7}$ cycloalkyl, 5-7 membered heterocycloalkyl, arylalkyl, heteroarylalkyl, ($C_{3-7}$ cycloalkyl)alkyl or (5-7 membered heterocycloalkyl)alkyl;

$R^8$ and $R^{12}$ are each, independently, H, $C_{1-8}$ alkyl, $C_{1-8}$ haloalkyl, $C_{2-8}$ alkenyl, $C_{2-8}$ alkynyl, aryl, heteroaryl, $C_{3-7}$ cycloalkyl, 5-7 membered heterocycloalkyl, arylalkyl, heteroarylalkyl, ($C_{3-7}$ cycloalkyl)alkyl, (5-7 membered heterocycloalkyl)alkyl, amino, ($C_{1-4}$ alkyl)amino, or di($C_{1-4}$ alkyl) amino;

$R^9$ and $R^{10}$ are each, independently, H, $C_{1-8}$ alkyl, $C_{2-8}$ alkenyl, $C_{2-8}$ alkynyl, aryl, heteroaryl, $C_{3-7}$ cycloalkyl, 5-7 membered heterocycloalkyl, arylalkyl, heteroarylalkyl, ($C_{3-7}$ cycloalkyl)alkyl, (5-7 membered heterocycloalkyl)alkyl, ($C_{1-8}$ alkyl)carbonyl, ($C_{1-8}$ haloalkyl)carbonyl, ($C_{1-8}$ alkoxy)carbonyl, ($C_{1-8}$ haloalkoxy)carbonyl, ($C_{1-4}$ alkyl)sulfonyl, ($C_{1-4}$ haloalkyl)sulfonyl or arylsulfonyl;

or $R^9$ and $R^{10}$, together with the N atom to which they are attached form a 5-7 membered heterocycloalkyl group;

$R^{13}$ and $R^{14}$ are each, independently, H, $C_{1-8}$ alkyl, $C_{2-8}$ alkenyl, $C_{2-8}$ alkynyl, aryl, heteroaryl, $C_{3-7}$ cycloalkyl, 5-7 membered heterocycloalkyl, arylalkyl, heteroarylalkyl, ($C_{3-7}$ cycloalkyl)alkyl, (5-7 membered heterocycloalkyl)alkyl, ($C_{1-8}$ alkyl)carbonyl, ($C_{1-8}$ haloalkyl)carbonyl, ($C_{1-8}$ alkoxy)carbonyl, ($C_{1-8}$ haloalkoxy)carbonyl, ($C_{1-4}$ alkyl)sulfonyl, ($C_{1-4}$ haloalkyl)sulfonyl or arylsulfonyl;

or $R^{13}$ and $R^{14}$, together with the N atom to which they are attached form a 5-7 membered heterocycloalkyl group;

Pr is an amino protecting group;

$R^N$ is H;

or Pr and $R^N$ together with the N atom to which they are attached form a cyclic amino protecting group;

$R^{2a}$ and $R^{2b}$ are each, independently, $C_{1-4}$ alkyl;

R and R' are each, independently, $C_{1-6}$ alkyl, arylalkyl or alkylaryl, or R and R' together with the O atoms to which they are attached and the intervening CH group form a 5- or 6-membered heterocycloalkyl group;

Y is an isocyanate group (—NCO) or isocyanate equivalent; and

Z is an isocyanate group (—NCO) or isocyanate equivalent.

In some embodiments, $R^{1a}$, $R^{1b}$, $R^{1c}$, $R^{1d}$, and $R^{1e}$ are each, independently, H, halo, cyano, nitro, $C_{1-6}$ alkyl, $C_{1-6}$ haloalkyl, $C_{2-6}$ alkenyl, $C_{2-6}$ alkynyl, $OR^7$, $SR^7$, $SOR^8$, $SO_2R^8$, $COR^8$, $COOR^7$, $OC(O)R^8$, $NR^9R^{10}$, carbocyclyl optionally substituted by one or more $R^6$ or heterocyclyl optionally substituted by one or more $R^6$.

In some embodiments, $R^{1a}$, $R^{1b}$, $R^{1c}$, $R^{1d}$, and $R^{1e}$ are each, independently, H, halo, cyano, nitro, $C_{1-6}$ alkyl, $C_{1-6}$ haloalkyl, $C_{2-6}$ alkenyl, $C_{2-6}$ alkynyl, $OR^7$ or carbocyclyl optionally substituted by one or more $R^6$.

In some embodiments, $R^{1a}$, $R^{1b}$, $R^{1c}$, $R^{1d}$, and $R^{1e}$ are each, independently, H, halo, $C_{1-6}$ alkyl, $C_{1-6}$ haloalkyl, $C_{1-6}$ alkyl, or $C_{1-6}$ haloalkyl.

In some embodiments, $R^{1a}$, $R^{1b}$, $R^{1c}$, $R^{1d}$, and $R^{1e}$ are each, independently, H, F, Cl, Br, or I.

In some embodiments, $R^{1a}$ is H or halo, $R^{1b}$ is H, $R^{1c}$ is halo, $R^{1d}$ is H, and $R^{1e}$ is H.

In some embodiments, $R^{1a}$ is halo, $R^{1b}$ is H, $R^{1c}$ is halo, $R^{1d}$ is H, and $R^{1e}$ is H.

In some embodiments:
$R^{1a}$ is F, $R^{1b}$ is H, $R^{1c}$ is F, $R^{1d}$ is H, and $R^{1e}$ is H;
$R^{1a}$ is H, $R^{1b}$ is H, $R^{1c}$ is Cl, $R^{1d}$ is H, and $R^{1e}$ is H;
$R^{1a}$ is H, $R^{1b}$ is H, $R^{1c}$ is F, $R^{1d}$ is H, and $R^{1e}$ is H; or
$R^{1a}$ is H, $R^{1b}$ is H, $R^{1c}$ is Cl, $R^{1d}$ is H, and $R^{1e}$ is H.

In some embodiments, $R^2$ is methyl or ethyl.

In some embodiments, $R^2$ is methyl.

In some embodiments, $R^3$ is Cl or Br.

In some embodiments, $R^3$ is Br.

In some embodiments, $R^4$ is halo, cyano, nitro, $C_{1-6}$ alkyl, $C_{1-6}$ haloalklyl, $C_{2-6}$ alkenyl, $C_{2-6}$ alkynyl, $C_{1-6}$ alkoxy, wherein said $C_{1-6}$ alkoxy group is optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms.

In some embodiments, $R^4$ is $C_{1-6}$ alkoxy optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms.

In some embodiments, $R^4$ is $C_{1-6}$ alkoxy.

In some embodiments, $R^4$ is $C_{1-3}$ alkoxy.

In some embodiments, $R^4$ is methoxy or ethoxy.

In some embodiments, $R^4$ is methoxy.

In some embodiments, $R^5$ is H, halo, cyano, nitro, $C_{1-6}$ alkyl, $C_{1-6}$ haloalkyl, $C_{2-6}$ alkenyl, $C_{2-6}$ alkynyl, or $C_{1-6}$ alkoxy.

In some embodiments, $R^5$ is H.

In some embodiments, R and R' are both $C_{1-4}$ alkyl.

In some embodiments, R and R' are both methyl.

In some embodiments, $R^{2a}$ and $R^{2b}$ are both methyl.

In some embodiments, Pr is an acyl group.

In some embodiments, Pr is —C(O)—($C_{1-4}$ alkyl).

In some embodiments, Pr is —C(O)Me.

In some embodiments:

$R^{1a}$, $R^{1b}$, $R^{1c}$, $R^{1d}$, and $R^{1e}$ are each, independently, H, halo, cyano, nitro, $C_{1-6}$ alkyl, $C_{1-6}$ haloalkyl, $C_{2-6}$ alkenyl, $C_{2-6}$ alkynyl, $OR^7$, $SR^7$, $SOR^8$, $SO_2R^8$, $COR^8$, $COOR^7$, $OC(O)R^8$, $NR^9R^{10}$, carbocyclyl optionally substituted by one or more $R^6$ or heterocyclyl optionally substituted by one or more $R^6$;

$R^3$ is F, Cl, Br or I;

$R^4$ is halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, wherein said $C_{1-6}$ alkoxy group is optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms; and $R^5$ is H, halo, cyano, nitro, $C_{1-6}$ alkyl, $C_{1-6}$ haloalkyl, $C_{2-6}$ alkenyl, $C_{2-6}$ alkynyl, or $C_{1-6}$ alkoxy.

In some embodiments:

$R^{1a}$, $R^{1b}$, $R^{1c}$, $R^{1d}$, and $R^{1e}$ are each, independently, H, halo, $C_{1-6}$ alkyl, $C_{1-6}$ haloalkyl, $C_{1-6}$ alkyl, or $C_{1-6}$ haloalkyl;

$R^3$ is F, Cl, Br or I;

$R^4$ is $C_{1-6}$ alkoxy group optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms; and $R^5$ is H.

In some embodiments:

$R^{1a}$, $R^{1b}$, $R^{1c}$, $R^{1d}$, and $R^{1e}$ are each, independently, H, F, Cl, Br or I;

$R^2$ is methyl or ethyl;

$R^3$ is F, Cl, Br or I;

$R^4$ is $C_{1-6}$ alkoxy; and $R^5$ is H.

In some embodiments:

$R^{1a}$, $R^{1b}$, $R^{1c}$, $R^{1d}$, and $R^{1e}$ are each, independently, H, F, or Cl;

$R^2$ is methyl;

$R^3$ is Cl or Br;

$R^4$ is methoxy; and $R^5$ is H.

In some embodiments:

$R^{1a}$ is F;
$R^{1b}$ is H;
$R^{1c}$ is F;
$R^{1d}$ is H;
$R^{1e}$ is H;
$R^2$ is methyl;
$R^3$ is Br;
$R^4$ is methoxy; and
$R^5$ is H.

In some embodiments:

$R^{1a}$ is H;
$R^{1b}$ is H;
$R^{1c}$ is Cl;
$R^{1d}$ is H;
$R^{1e}$ is H;
$R^2$ is methyl;
$R^3$ is Br;
$R^4$ is methoxy; and
$R^5$ is H.

In some embodiments:

$R^{1a}$ is H;
$R^{1b}$ is H;
$R^{1c}$ is F;
$R^{1d}$ is H;
$R^{1e}$ is H;
$R^2$ is methyl;
$R^3$ is Br;
$R^4$ is methoxy; and
$R^5$ is H.

In some embodiments:

$R^{1a}$ is H;
$R^{1b}$ is H;
$R^{1c}$ is Cl;
$R^{1d}$ is H;
$R^{1e}$ is H;
$R^2$ is methyl;
$R^3$ is Cl;
$R^4$ is methoxy; and
$R^5$ is H.

In some embodiments, Z is —NCO.

In some embodiments, Y is —NCO.

In some embodiments:

$R^3$ is F, Cl, Br or I;

$R^4$ is halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, wherein said $C_{1-6}$ alkoxy group is optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms; and $R^5$ is H, halo, cyano, nitro, $C_{1-6}$ alkyl, $C_{1-6}$ haloalkyl, $C_{2-6}$ alkenyl, $C_{2-6}$ alkynyl, or $C_{1-6}$ alkoxy.

In some embodiments:

$R^3$ is F, Cl, Br or I;

$R^4$ is $C_{1-6}$ alkoxy group optionally substituted with one or more $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ thioalkoxy, $C_{1-4}$ alkylureido, amino, ($C_{1-6}$ alkoxy)carbonyl, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ halothioalkoxy, hydroxyl, nitro or phenyl optionally substituted with 1 to 5 halogen atoms; and $R^5$ is H.

In some embodiments:

$R^2$ is methyl or ethyl;

$R^3$ is F, Cl, Br or I;

$R^4$ is $C_{1-6}$ alkoxy; and $R^5$ is H.

In some embodiments:

$R^2$ is methyl;

$R^3$ is Cl or Br;

$R^4$ is methoxy; and $R^5$ is H.

In some embodiments, for compounds of Formula (IIc), $R^2$ is methyl; $R^3$ is Cl or Br; $R^4$ is methoxy; and $R^5$ is H.

In some embodiments, for compounds of Formula (IVa), $R^2$ is methyl; $R^3$ is Br; $R^4$ is methoxy; $R^5$ is H; and Pr is —C(O)Me.

In some embodiments, for compounds of Formula (IVa), $R^2$ is methyl; $R^3$ is Cl; $R^4$ is methoxy; $R^5$ is H; and Pr is —C(O)Me.

In some embodiments, for compounds of Formula (Vb), $R^2$ is methyl; $R^4$ is methoxy; $R^5$ is H; and Pr is —C(O)Me.

In some embodiments, for compounds of Formula (VIa), $R^{2a}$ is methyl; $R^{2b}$ is methyl; $R^4$ is methoxy; $R^5$ is H; and Pr is —C(O)Me.

Urea Forming Step

The chemical reactions resulting in compounds of Formula (I) and formation of the urea linkage can be carried out by any of numerous methods known in the art. Example urea-forming processes according to the present invention are depicted in Schemes Ia and Ic. Accordingly, the compound of Formula (I):

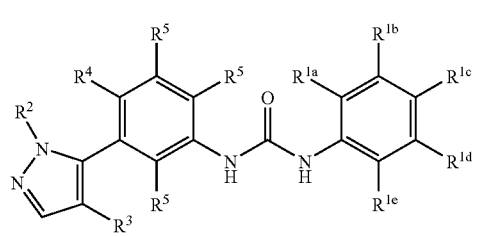

wherein constituent members are defined herein, can be prepared by:

reacting a compound of Formula (II):

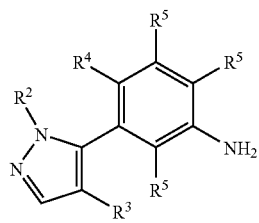

with a compound of Formula (III):

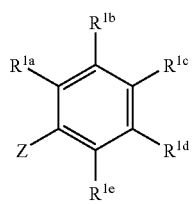

wherein Z is an isocyanate group (—NCO) or isocyanate equivalent, for a time and under conditions suitable for forming the compound of Formula (I); or reacting a compound of Formula (II) with an isocyanate-generating reagent for a time an under conditions suitable for forming a compound of Formula (IIa):

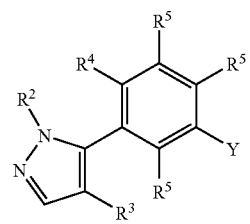

wherein Y is an isocyanate group or isocyanate equivalent; and reacting the compound of Formula (IIa) with a compound of Formula (IIIa):

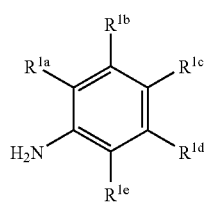

for a time and under conditions suitable for forming the compound of Formula (I).

In some embodiments, the reactants are of Formulae (II) and (III).

In some embodiments, the urea-forming processes according to the present invention are depicted in Scheme Ic to give compounds of Formula (Ia). Accordingly, in some embodiments the compound of Formula (Ia):

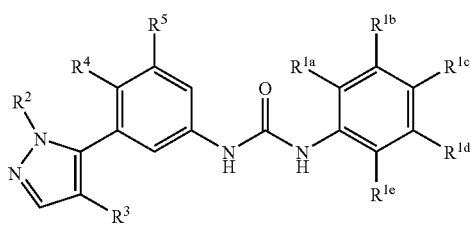

(Ia)

wherein constituent members are defined herein, can be prepared by:

reacting a compound of Formula (IIc):

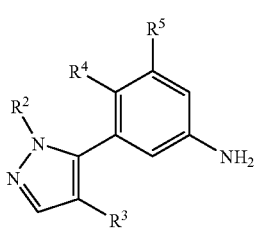

(IIc)

with a compound of Formula (III):

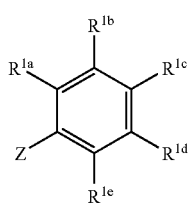

(III)

wherein Z is an isocyanate group (—NCO) or isocyanate equivalent, for a time and under conditions suitable for forming the compound of Formula (Ia); or reacting a compound of Formula (IIc) with an isocyanate-generating reagent for a time an under conditions suitable for forming a compound of Formula (IId):

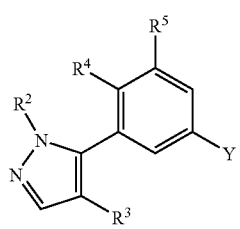

(IId)

wherein Y is an isocyanate group or isocyanate equivalent; and reacting the compound of Formula (IIa) with a compound of Formula (IIIa):

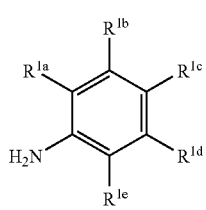

(IIIa)

for a time and under conditions suitable for forming the compound of Formula (Ia).

In some embodiments, the reactants are of Formulae (IIc) and (III).

In some embodiments, the reactants bearing the isocyante or isocyanate equivalent groups (e.g., compounds of Formula (IIa) or (III)) are provided in excess relative to the amount of aniline (e.g., compounds of Formula (II) or (IIIa)). For example, the molar ratio of a compound of Formula (II) to a compound of Formula (III), or the molar ratio of a compound of Formula (IIIa) to a compound of Formula (IIa), can be about 1:1 to about 1:1.5 or about 1:1 to about 1:1.2. In further embodiments, the compound having the isocyanate or isocyante equivalent moieties can be added to a solution containing the aniline. The addition can be, for example, carried out in a portionwise manner.

In some embodiments, the reactants bearing the isocyante or isocyanate equivalent groups (e.g., compounds of Formula (IId) or (III)) are provided in excess relative to the amount of aniline (e.g., compounds of Formula (IIc) or (IIIa)). For example, the molar ratio of a compound of Formula (IIc) to a compound of Formula (III), or the molar ratio of a compound of Formula (IIIa) to a compound of Formula (IId), can be about 1:1 to about 1:1.5 or about 1:1 to about 1:1.2. In further embodiments, the compound having the isocyanate or isocyante equivalent moieties can be added to a solution containing the aniline. The addition can be, for example, carried out in a portionwise manner.

The urea formation step can be optionally carried out in the presence of organic solvent such as an aromatic solvent (e.g., benzene, toluene, etc.), N,N-dimethylformamide (DMF), methylsulfoxide, acetonitrile, ethyl acetate, methylene chloride, mixtures thereof and the like. In some embodiments, the reaction solvent contains toluene.

The urea-forming reaction can be carried out at any temperature. For example, suitable temperatures can be from about 0 to about 60° C. or about 10 to about 45° C. In some embodiments, the reaction is carried out at a reduced temperature such as about 10 to about 20° C. In some embodiments, urea formation is carried out under an inert atmosphere.

In some embodiments, the aniline starting material (e.g., a compound of Formula (II) or (IIIa)) can be dissolved in an aromatic solvent prior to the reacting, forming a solution. The aromatic solvent can be refluxed for a time and under conditions to at least partially remove residual water optionally present in the solution. Removal of water is believed to diminish formation of unwanted byproducts and increase yields. In some embodiments, the water present in the solution after refluxing is less than about 5, less than about 3, less than about 1, less than about 0.1, less than about 0.03 or less than about 0.01% by volume.

In some embodiments, the aniline starting material (e.g., a compound of Formula (IIc) or (IIIa)) can be dissolved in an aromatic solvent prior to the reacting, forming a solution. The aromatic solvent can be refluxed for a time and under conditions to at least partially remove residual water optionally present in the solution. Removal of water is believed to diminish formation of unwanted byproducts and increase yields. In some embodiments, the water present in the solution after refluxing is less than about 5, less than about 3, less than about 1, less than about 0.1, less than about 0.03 or less than about 0.01% by volume.

In some embodiments, the compound of Formula (I) is prepared by reacting a compound of Formula (II) with a compound of Formula (III). In alternate embodiments, the compound of Formula (I) is prepared by reacting a compound of Formula (IIa) with a compound of Formula (IIIa).

In some embodiments, the compound of Formula (Ia) is prepared by reacting a compound of Formula (IIc) with a compound of Formula (III). In alternate embodiments, the compound of Formula (Ia) is prepared by reacting a compound of Formula (IId) with a compound of Formula (IIIa).

Starting materials bearing isocyanate and isocyanate equivalent moieties are well known in the art and commercially available. These can also be routinely prepared from corresponding anilines by reaction with an isocyanate-generating reagent, which includes materials that react with the amino group of an aniline to form an isocyanate equivalent group. For example, an isocyanate-bearing compound can be readily prepared by reacting the corresponding aniline with an isocyanate-generating reagent such as, for example, phosgene (i.e., $Cl_2C=O$) or triphosgene [i.e., bis-trichloromethyl carbonate, $Cl_3COC(O)OCCl_3$] to generate the isocyanate derivative which can then be optionally isolated. Another procedure for preparing isocyanates involves using the isocyanate-generating reagent di-t-butyltricarbonate to generate isocyanates from anilines in a similar manner as described above. An example of this procedure is reported by Peerlings et al. in *Tetrahedron Lett.* 1999, 40, 1021-1024, the disclosure of which is incorporated herein by reference in its entirety. These procedures and others known in the art can give rise to isocyanates as illustrated in Schemes IIa, IIb and IIc below.

Scheme IIa

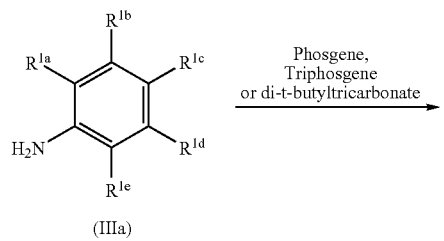

(IIIa)

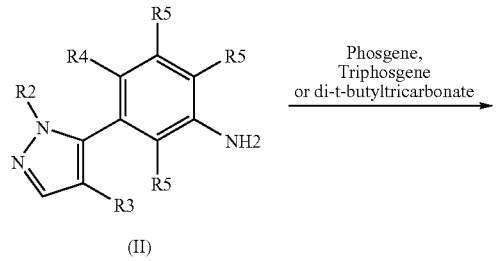

(II)

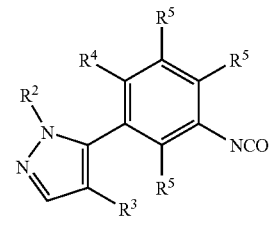

Scheme IIc

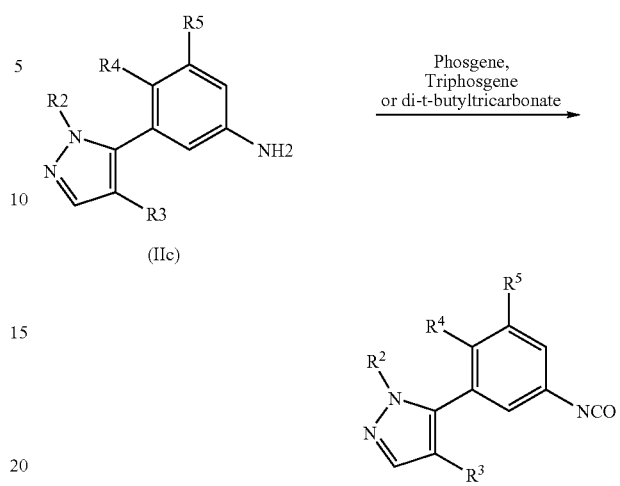

(IIc)

An isocyanate equivalent include a moiety other than isocyanate that is able to form a urea linkage upon reaction with an aniline (e.g., compounds of Formulae (II), (IIc), and (IIIa)). Isocyanate equivalents can be prepared from the corresponding anilines by the sequential action of the isocyante-generating reagents: 1) carbonyl diimidazole and 2) methyl iodide in THF and acetonitrile, respectively, as described, for example, by Batey et al. in *Tetrahedron Lett.* 1998, 39, 6267-6270, the disclosure of which is incorporated herein by reference in its entirety. This procedure can give rise to isocyanate equivalents as illustrated in Schemes IIIa, IIIb and IIIc below.

Scheme IIIa

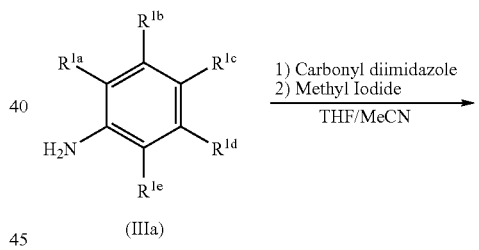

(IIIa)

Scheme IIIb

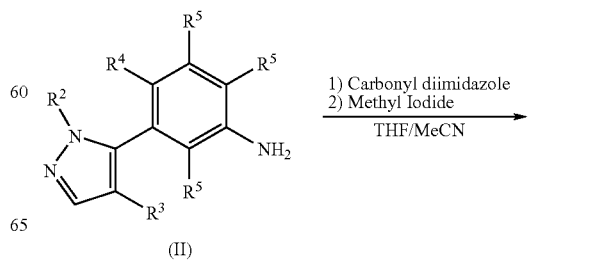

(II)

-continued

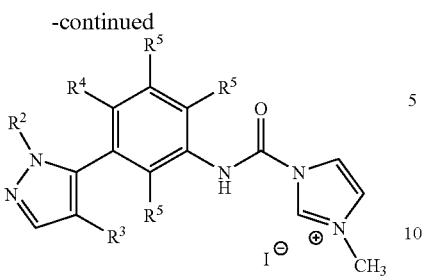

(IIc)

Scheme IIIc

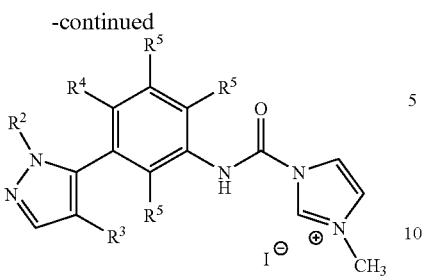

Other isocyanate equivalents can be generated by reacting the corresponding aniline with an isocyanate-generating reagent such a substituted alkyl chloroformate of Formula:

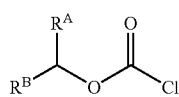

wherein $R^A$ is $C_{1-8}$ alkyl and $R^B$ is a leaving group, for a time and under conditions suitable for forming the isocyanate equivalent. In some embodiments, $R^A$ is methyl. In further embodiments, $R^B$ is Cl, Br, I, mesylate, tosylate or the like. In yet further embodiments, $R^B$ is Cl, Br or I; and in yet further embodiments, $R^B$ is Cl.

Formation of isocyanate equivalents using a substituted alkyl chloroformate is illustrated in Schemes IVa, IVb and IVc below.

Scheme IVa

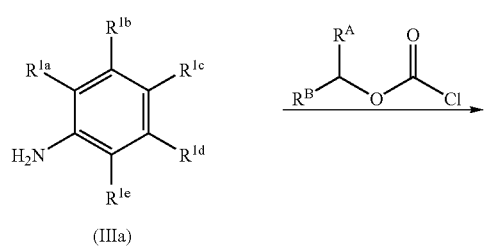

(IIIa)

-continued

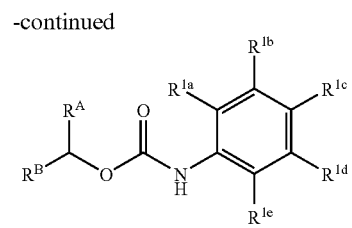

Scheme IVb

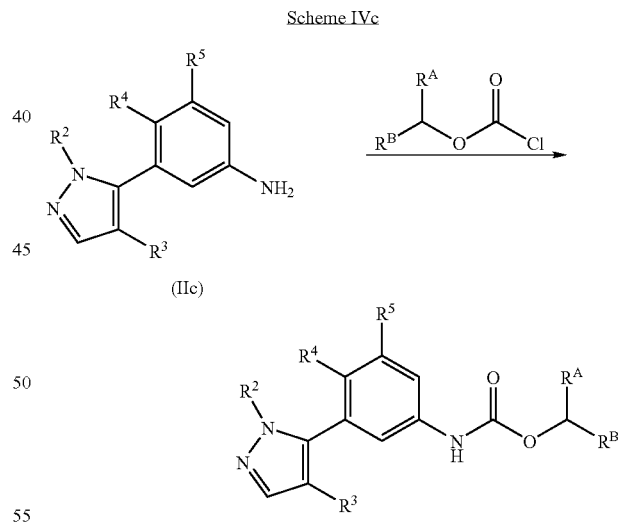

(II)

Scheme IVc

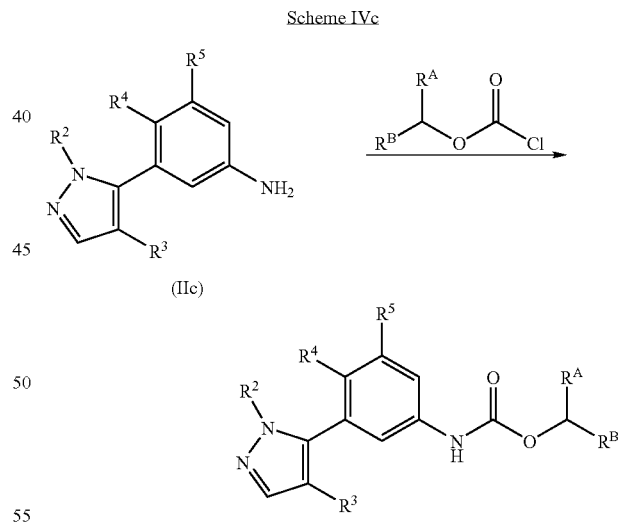

(IIc)

Reaction of anilines (e.g., compounds of Formula (II), (IIc) and (IIIa)) such as according to Schemes IVa, IVb and IVc with the isocyanate-generating reagent substituted alkylchloroformate can be optionally carried out in the presence of an organic base. Suitable organic bases include, for example, pyridine, dimethylaminopyridine, piperidine, morpholine, mixtures thereof and the like. In some embodiments, the organic base is pyridine. The organic base can, in some instances, replace the leaving group $R^B$ to form an organic base derivative. In some embodiments, pyridine replaces the leaving group $R^B$ to form a pyridinium derivative.

The reactions of anilines (e.g., compounds of Formula (II), (IIc), and (IIIa)) with substituted alkylchloroformates can be optionally carried out in a solvent. Suitable solvents include, for example, polar solvents such as N,N-dimethylformamide (DMF), methysulfoxide, acetonitrile, ethyl acetate, tetrahydrofuran, methylene chloride and the like.

Generally, the molar ratio of an aniline, such as a compound of Formula (II), (IIc), or (IIIa), to a substituted alkylchloroformate can range from about 1:1 to about 1:2. In some embodiments, the ratio is about 1:1 to about 1:1.5. Such reactions can be carried out at any suitable temperature such as, for example, about 0 to about 60° C. or about 10 to about 45° C.

It is generally understood that although the isocyanate or isocyanate equivalent can be isolated, it can also be generated in situ and used directly to complete the urea formation reaction. Accordingly, in some embodiments, the isocyanate or isocyanate equivalent is generated in situ and reacted directly with the appropriate aniline without isolation.

Deprotection

According to a further aspect of the invention, a compound of Formula (II) can be prepared by the process comprising reacting a compound of Formula (IV):

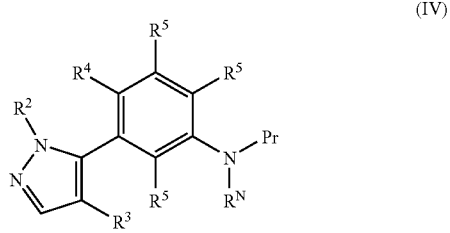

(IV)

wherein constituent members are provided herein, with a deprotecting agent for a time and under conditions suitable for forming the compound of Formula (II).

In some embodiments, the compounds of Formula (IIc) can be prepared by the process comprising reacting a compound of Formula (IVa):

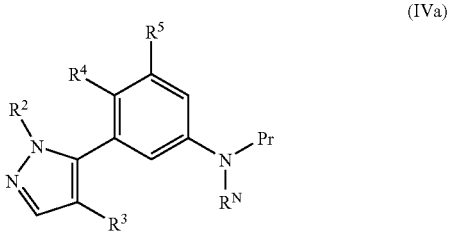

(IVa)

wherein constituent members are provided herein, with a deprotecting agent for a time and under conditions suitable for forming the compound of Formula (IIc).

Numerous suitable deprotecting agents are known that can selectively remove an amino protecting group. The chemistry of protecting groups can be found, for example, in Green and Wuts, *Protective Groups in Organic Synthesis*, 3rd. Ed., Wiley & Sons, 1999, which is incorporated herein by reference in its entirety. In some embodiments, the amino protecting group (Pr) is selectively removed by hydrolysis. In further embodiments, the deprotecting agent is a base such as an inorganic base. An example deprotecting reagent is a base containing hydroxide, such as an alkali metal hydroxide including sodium hydroxide, lithium hydroxide, potassium hydroxide and the like. In some embodiments, the deprotecting agent is sodium hydroxide.

Deprotection can be optionally carried out in an organic solvent. In some embodiments, the organic solvent contain an alcohol such as methanol, ethanol, isopropanol, n-propanol, butanol, mixtures thereof or the like. In some embodiments, the organic solvent contains methanol.

Deprotection can be conducted at any suitable temperature. In some embodiments, deprotection is carried out at a temperature at or above about room temperature. In some embodiments, deprotection is carried out at about 0 to about 100, about 20 to about 100, about 30 to about 100, about 40 to about 100, about 50 to about 100 or about 70 to about 90° C. In further embodiments, deprotection is carried out at reflux temperature.

In some embodiments, the deprotecting reagent can be provided in molar excess relative to the amount of compound of Formula (IV). In embodiments where the deprotecting reagent is an alkali metal hydroxide the molar ratio of alkali metal hydroxide to compound of Formula (IV) is about 1:1 to about 1:100, about 1:1 to about 1:10, about 1:3 to about 1:8, or about 1:4 to about 1:6.

In some embodiments, the deprotecting reagent can be provided in molar excess relative to the amount of compound of Formula (IVa). In embodiments where the deprotecting reagent is an alkali metal hydroxide the molar ratio of alkali metal hydroxide to compound of Formula (IVa) is about 1:1 to about 1:100, about 1:1 to about 1:10, about 1:3 to about 1:8, or about 1:4 to about 1:6.

The deprotection of compounds of Formula (IV) can optionally be carried out in the presence of a compound of Formula (V)

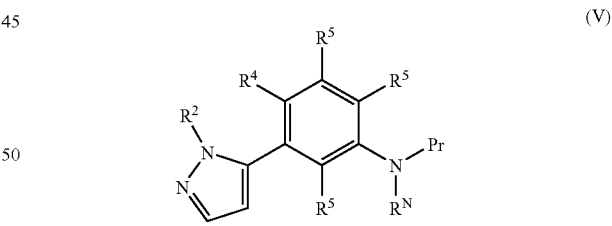

(V)

which can be present in batches of compound of Formula (IV) due to any number of reasons including, for example, incomplete halogenation of the compound of Formula (V) or dehalogenation of the compound of Formula (IV) during work up, isolation, or other manipulations. Compositions of the starting material of Formula (IV) can optionally contain the compound of Formula (V) in any mole % such as, for example, less than about 10, less than about 8, less than about 5, less than about 4, less than about 3, less than about 2 or less than about 1 mole %. Deprotection of a compound of Formula (V) can result in formation of the corresponding non-halogenated (i.e. lacking $R^3$), free amine of Formula (IIb):

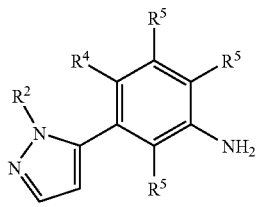
(IIb)

Accordingly, the product of the deprotection reaction can contain some amount of compound of Formula (IIb). In some embodiments, the product of the deprotection reaction contains less than about 10, less than about 8, less than about 5, less than about 4, less than about 3, less than about 2 or less than about 1 mole % of a compound of Formula (IIb).

In some embodiments, the deprotection of compounds of Formula (IVa) can optionally be carried out in the presence of a compound of Formula (Vb)

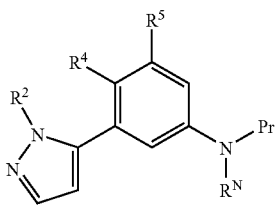
(Vb)

which can be present in batches of compound of Formula (IVa) due to any number of reasons including, for example, incomplete halogenation of the compound of Formula (Vb) or de-halogenation of the compound of Formula (IVa) during work up, isolation, or other manipulations. Compositions of the starting material of Formula (IVa) can optionally contain the compound of Formula (Vb) in any mole % such as, for example, less than about 10, less than about 8, less than about 5, less than about 4, less than about 3, less than about 2 or less than about 1 mole %. Deprotection of a compound of Formula (Vb) can result in formation of the corresponding non-halogenated (i.e. lacking R³), free amine of Formula (IIe):

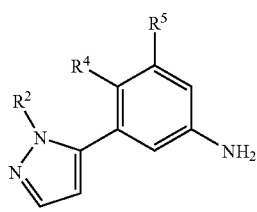
(IIe)

Accordingly, the product of the deprotection reaction can contain some amount of compound of Formula (IIe). In some embodiments, the product of the deprotection reaction contains less than about 10, less than about 8, less than about 5, less than about 4, less than about 3, less than about 2 or less than about 1 mole % of a compound of Formula (IIe).

Halogenation

In further aspects of the invention, a compound of Formula (IV) can be prepared by the process comprising reacting a compound of Formula (V):

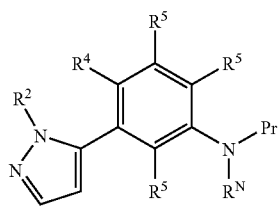
(V)

with a halogenating reagent for a time and under conditions suitable for forming the compound of Formula (IV).

In some embodiments of the invention, compounds of Formula (IVa) can be prepared by the process comprising reacting a compound of Formula (Vb):

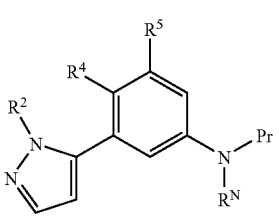
(Vb)

with a halogenating reagent for a time and under conditions suitable for forming the compound of Formula (IVa).

Any of numerous halogenating reagents known in the art can be used. In some embodiments, the halogenating reagent is a brominating or chlorinating reagent. Some example brominating reagents include, for example, $Br_2$, N-bromosuccinimide (NBS), 1,3-dibromo-5,5-dimethylhydantoin, pyridinium tribromide ($pyrHBr_3$) and the like. An example chlorinating reagent is N-chlorosuccinimide. In some embodiments, the halogenating reagent is N-bromosuccinimide.

Any suitabable organic solvent can be optionally used to carry out the halogenating reaction. In some embodiments, the organic solvent contains an alcohol such as methanol, ethanol, n-propanol, isopropanol, butanol, mixtures thereof and the like. In some embodiments, the organic solvent is methanol. In further embodiments, the organic solvent includes dimethylformamide or tetrahydrofuran.

Suitable temperatures for the halogenating reaction can vary. For example, the reaction temperature can be at or below about room temperature such as, for example, from about 0 to about 25° C.

The molar ratio of halogenating reagent to compound of Formula (V) can be routinely selected or optimized by the skilled artisan to miminize di-halogenated by products and maximize yield of the mono-halogenated product. In some embodiments, the molar ratio is from about 1:0.8 to about 1:1.2, from about 1:0.9 to about 1:1.1, from about 1:0.95 to about 1:1.05, or about 1:1.

The molar ratio of halogenating reagent to compound of Formula (Vb) can be routinely selected or optimized by the skilled artisan to miminize di-halogenated by products and maximize yield of the mono-halogenated product. In some embodiments, the molar ratio is from about 1:0.8 to about 1:1.2, from about 1:0.9 to about 1:1.1, from about 1:0.95 to about 1:1.05, or about 1:1.

Cyclization

In yet further aspects of the invention, a compound of Formula (V) can be prepared by the process comprising reacting a compound of Formula (VI):

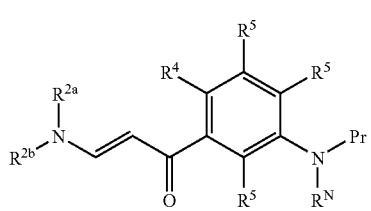

(VI)

with an alkylhydrazine having the formula $NH_2NH-R^2$ for a time and under conditions suitable for forming the compound of Formula (V).

In some embodiments, compounds of Formula (Vb) can be prepared by the process comprising reacting a compound of Formula (VIa):

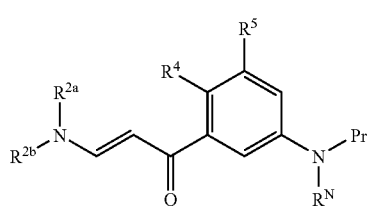

(VIa)

with an alkylhydrazine having the formula $NH_2NH-R^2$ for a time and under conditions suitable for forming the compound of Formula (Vb).

In some embodiments, the alkylhydrazine is methyl hydrazine ($NH_2NH-Me$).

The cyclization reaction can be optionally carried out in the presence of an organic solvent. In some embodiments, the solvent contains an alcohol such as, for example, methanol, ethanol, isopropanol, n-propanol, butanol, mixtures thereof and the like. In some embodiments, the organic solvent contains methanol. In some embodiments, the organic solvent contains ethanol. In further embodiments, excess alkylhydrazine can serve as solvent.

The cyclization reaction can further be carried out in the presence of an acid. In some embodiments, the acid is an inorganic acid such as hydrochloric acid, hydrobromic acid; or the acid is an organic acid such as acetic acid or trifluoroacetic acid. In some embodiments, the acid is hydrochloric acid. The molar ratio of the alkylhydrazine to acid is from about 1:0.1 to about 1:100; from about 1:0.1 to about 1:20, from about 1:0.5 to about 1:12, from about 1:1 to about 1:8, or from about 1:2 to about 1:6. In some embodiments, the molar ratio of the alkylhydrazine to acid is about 1:3. In further embodiments, the molar ratio of the alkylhydrazine to acid is above about 1:2.

The molar ratio of compound of Formula (VI) to alkylhydrazine can vary. In some embodiments, alkylhydrazine can be provided in molar excess. Example suitable molar ratios include about 1:1 to about 1:10, about 1:1 to about 1:5, about 1:1 to about 1:3, about 1:1 to about 1:1.5 or about 1:1 to about 1:1.2.

The molar ratio of compound of Formula (VIa) to alkylhydrazine can vary. In some embodiments, alkylhydrazine can be provided in molar excess. Example suitable molar ratios include about 1:1 to about 1:10, about 1:1 to about 1:5, about 1:1 to about 1:3, about 1:1 to about 1:1.5 or about 1:1 to about 1:1.2.

The cyclization reaction can be carried out at any temperature. In some embodiments, the reaction temperature is at or below room temperature. In further embodiments, the reaction temperature is from about −10 to about 30° C. In yet further embodiments, the reaction temperature is initially held at about −10 to about 0° C., after which the temperature is then held for a period of time at about 5 to about 15° C., after which the temperature is then held at about 20 to about 25° C.

In some embodiments, the cyclization reaction can be conducted such that the compound of Formula (VI) is added to a solution containing the alkylhydrazine and optionally an acid, such as HCl.

In some embodiments, the cyclization reaction can be conducted such that the compound of Formula (VIa) is added to a solution containing the alkylhydrazine and optionally an acid, such as HCl.

The reacting with an alkylhydrazine can optionally further produce a byproduct compound of Formula (Va):

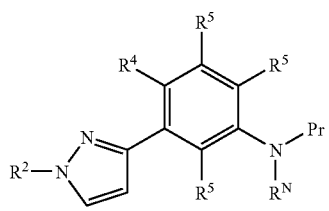

(Va)

In some embodiments, the compound of Formula (Va) is produced in a lesser amount than the compound of Formula (V). For example, the cyclization reaction can result in a product having molar ratio of compound of Formula (V) to compound of Formula (Va) that is greater than about 2, greater than about 4, or greater than about 5.

In some embodiments, the optionally further produced byproduct compound is of Formula (Vc):

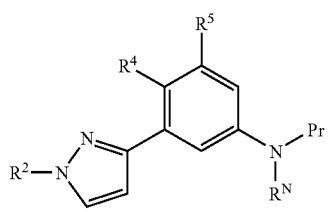

(Vc)

In some embodiments, the compound of Formula (Vc) is produced in a lesser amount than the compound of Formula (Vb). For example, the cyclization reaction can result in a product having molar ratio of compound of Formula (Vb) to compound of Formula (Vc) that is greater than about 2, greater than about 4, or greater than about 5.

Condensation

In yet a further aspect of the present invention, a compound of Formula (VI) is prepared by the process comprising reacting a compound of Formula (VII):

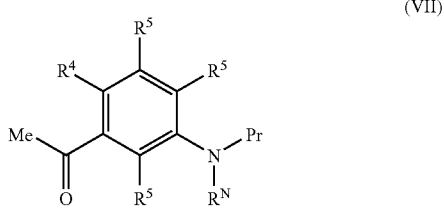

(VII)

with an acetal of Formula (VIII):

(VIII)

wherein R and R' are each, independently, $C_{1-6}$ alkyl, arylalkyl or alkylaryl, or R and R' together with the O atoms to which they are attached and the intervening CH group form a 5- or 6-membered heterocycloalkyl group, for a time and under conditions suitable for forming the compound of Formula (VI).

In some embodiments, a compound of Formula (VIa) is prepared by the process comprising reacting a compound of Formula (VIIa):

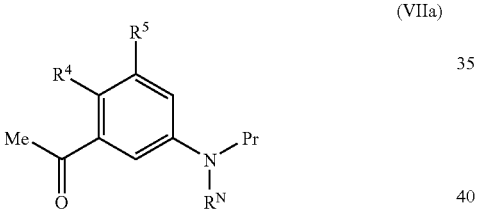

(VIIa)

with an acetal of Formula (VIII), as described herein.

The acetal of Formula (VIII) can be any of a variety of compounds including, for example, N,N-dimethylformamide dimethyl acetal, N,N-dimethylformamide diethyl acetal, N,N-dimethylformamide dipropyl acetal, N,N-dimethylformamide diisopropyl acetal, N,N-dimethylformamide dibutyl acetal, N,N-dimethylformamide di-t-butyl acetal, and N,N-dimethylformamide dineopentyl acetal, N,N-dimethylformamide dicyclohexyl acetal, N,N-dimethylformamide dibenzyl acetal, N,N-dimethylformamide ethylene acetal and N,N,5,5-tetramethyl-1,3-dioxan-2-amine. In some embodiments, the acetal is N,N-dimethylformamide dimethyl acetal.

The condensation reaction can be optionally carried out in a solvent such as an organic solvent. In some embodiments, the solvent contains an alcohol such as methanol, ethanol, n-propanol, isopropanol, butanol, pentanol, mixtures thereof and the like. In some embodiments, the solvent is ethanol. In further embodiments, the solvent is methanol. In yet further embodiments, excess acetal can serve as solvent.

In some embodiments, the condensation reaction is carried out in the same solvent as the cyclization reaction. In further embodiments, the product of the condensation reaction is not isolated prior to carrying out the cyclization reaction.

The condensation reaction can be carried out at any suitable temperature such as at or above room temperature. In some embodiments, the reaction temperature is from about 20 to about 95° C., about 20 to about 85° C., or about 20 to about 75° C. In further embodiments, the reaction temperature is reflux temperature.

The condensation reaction can be optionally carried out such that the acetal of Formula (VIII) is added to a mixture of the compound of Formula (VII) and solvent. The mixture can be homogenous or heterogenous.

In some embodiments, the acetal is provided in molar excess relative to the amount of compound of Formula (VII). Example molar ratios of said acetal to compound of Formula (VII) include about 1.1 to about 10, about 1.2 to about 5, or about 1.5 to about 3.

The condensation reaction can be optionally carried out such that the acetal of Formula (VIII) is added to a mixture of the compound of Formula (VIIa) and solvent. The mixture can be homogenous or heterogenous.

In some embodiments, the acetal is provided in molar excess relative to the amount of compound of Formula (VIIa). Example molar ratios of said acetal to compound of Formula (VIIa) include about 1.1 to about 10, about 1.2 to about 5, or about 1.5 to about 3.

Process Intermediates

The present invention further provides process intermediates for Formulae (II), (IV), (V) and (VI):

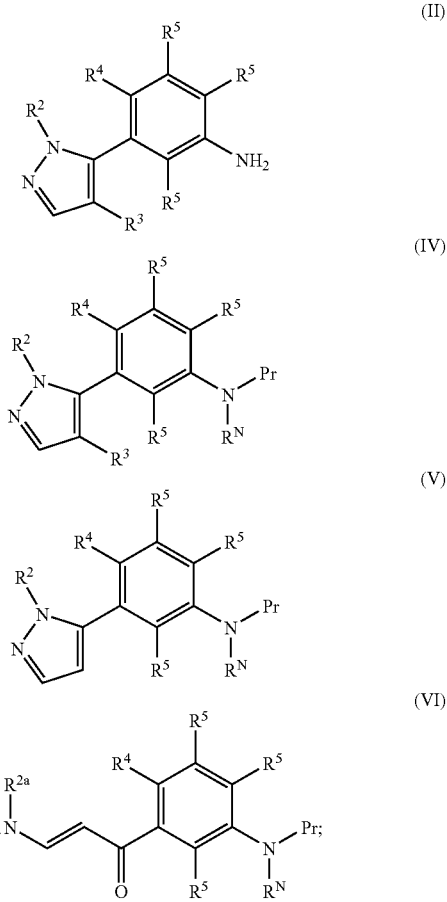

wherein constituent members are provided herein.

In some embodiments, two of the $R_5$ groups are H.

Some embodiments of the present invention provide process intermediates for Formulae (IIc), (IVa), (Vb) and (VIa):

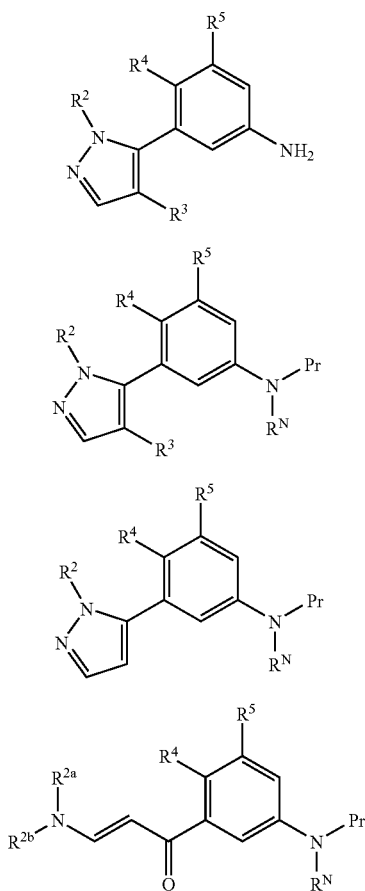

In some embodiments, R$_5$, at each occurrence is H.

Definitions

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and iso propyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, cyclohexenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

An alkyl group in which all of the hydrogen atoms are replaced with halogen atoms can be referred to as "perhaloalkyl."

As used herein, "carbocyclyl" refers to groups that are saturated (i.e., containing no double or triple bonds) or unsaturated (i.e., containing one or more double or triple bonds) cyclic hydrocarbon moieties. Carbocyclyl groups can be mono- or polycyclic. Example carbocyclyl groups include cyclopropyl, cyclobutyl, cyclopentyl, cyclohexyl, cycloheptyl, cyclopentenyl, 1,3-cyclopentadienyl, cyclohexenyl, norbomyl, norpinyl, norcamyl, adamantyl, phenyl, and the like. Carbocyclyl groups can be aromatic (e.g., "aryl") or non-aromatic (e.g., "cycloalkyl"). In some embodiments, carbocyclyl groups can have from 3 to about 20, 3 to about 10, or 3 to about 7 carbon atoms.

As used herein, "aryl" refers to monocyclic or polycyclic aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic hydrocarbons including cyclized alkyl, alkenyl, and alkynyl groups. Cycloalkyl groups can include mono-, bi- or polycyclic ring systems as well as double and triple bonds. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbomyl, norpinyl, norcamyl, adamantyl, and the like. Also included in the definition of cycloalkyl are moieties that have one or more aromatic rings fused (i.e., having a bond in common with) to the cycloalkyl ring, for example, benzo derivatives of pentane, hexane, and the like.

As used herein, "heterocyclyl" refers to a group that can be a saturated or unsaturated carbocyclyl group wherein one or more of the ring-forming carbon atoms of the carbocyclyl group is replaced by a heteroatom such as O, S, or N. Heterocyclyl groups can be aromatic (e.g., "heteroaryl") or non-aromatic (e.g., "heterocycloalkyl"). Heterocyclyl groups can correspond to hydrogenated and partially hydrogenated heteroaryl groups. Heterocarbocyclyl groups can contain, in addition to at least one heteroatom, from about 1 to about 20, about 2 to about 10, or about 2 to about 7 carbon atoms and can be attached through a carbon atom or heteroatom. In some embodiments, heterocyclyl groups can have from 3 to 20, 3 to 10, 3 to 7, or 5 to 7 ring-forming atoms. Further, heterocyclyl groups can be substituted or unsubstituted. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like as well as any of the groups listed for heteroaryl and heterocycloalkyl.

As used herein, "heteroaryl" groups are monocyclic and polycyclic aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-S-dioxide, benzoxazolin-2-on-yl, indolinyl, benzodioxolanyl, benzodioxane, and the like. In some embodiments, heteroaryl groups can have from 1 to about 20 carbon atoms, and in further embodiments from about 3 to about 20 carbon atoms. In some embodiments, heteroaryl groups have 1 to about 4, 1 to about 3, or 1 to 2 heteroatoms.

As used herein, "heterocycloalkyl" refers to a cycloalkyl group wherein one or more of the ring-forming carbon atoms is replaced by a heteroatom such as an O, S, N, or P atom. Also included in the definition of heterocycloalkyl are moieties that have one or more aromatic rings fused (i.e., having a bond in common with) to the nonaromatic heterocyclic ring, for example phthalimidyl, naphthalimidyl pyromellitic diimidyl, phthalanyl, and benzo derivatives of saturated heterocycles such as indolene and isoindolene groups.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to alkoxy substituted by at least one halo.

As used herein, "thioalkoxy" refers to an alkoxy group in which the O atom is replaced by an S atom.

As used herein, "halothioalkoxy" refers to thioalkoxy substituted by at least one halo.

As used herein, "acyl" refers to a carbonyl group substituted by H, alkyl, alkenyl, alkynyl or carbocyclyl. Example acyl groups include formyl or acetyl.

As used herein, "acyloxy" refers to —O-acyl.

As used herein, "carboxamide" or "aminocarbonyl" refers to —C(O)NH$_2$.

As used herein, "alkylcarboxamide" or "alkylaminocarbonyl" refers to —C(O)NH(alkyl).

As used herein, "dialkylcarboxamide" or "dialkylaminocarbonyl" refers to —C(O)N(alkyl)$_2$.

As used herein, "sulfonamide" refers to —S(O)NH$_2$.

As used herein, "alkylsulfonamide" refers to —S(O)NH(alkyl).

As used herein, "dialkylsulfonamide" refers to —S(O)N(alkyl)$_2$.

As used herein, "sulfonyl" refers to SO2.

As used herein, "sulfinyl" refers to SO.

As used herein, "alkylsulfinyl" refers to sulfinyl substituted by alkyl.

As used herein, "haloalkylsufinyl" refers to sulfinyl substituted by haloalkyl.

As used herein, "arylsulfinyl" refers to sulfinyl substituted by aryl.

As used herein, "alkylsulfonyl" refers to sulfonyl substituted by alkyl.

As used herein, "haloalkylsulfonyl" refers to sulfonyl substituted by haloalkyl.

As used herein, "arylsulfonyl" refers to sulfonyl substituted by aryl.

As used herein, "uerido" refers to —NHC(O)NH$_2$.

As used herein, "alkyluserido" refers to ureido substituted by an alkyl group.

As used herein, "amino" refers to NH2.

As used herein, "alkylamino" refers to amino substituted by alkyl.

As used herein, "dialkylamino" refers to amino substituted by two alkyl groups.

As used herein, "alkoxycarbonyl" refers to —CO-(alkoxy).

As used herein, "haloalkoxycarbonyl" refers to —CO-(haloalkoxy).

As used herein, "carbocyclylalkyl" refers to alkyl substituted by carbocyclyl.

As used herein, "arylalkyl" refers to an alkyl moiety substituted by an aryl group. Example aralkyl groups include benyl, phenethyl, and naphthylmethyl groups. In some embodiments, arylalkyl groups have from 7 to 20 or 7 to 11 carbon atoms.

As used herein, "heterocyclylalkyl" refers to alkyl substituted by hetercyclyl.

As used herein, "heterocycloalkylalkyl" refers to alkyl substituted by heterocycloalkyl.

As used herein, the term "reacting" is used as known in the art and generally refers to the bringing together of chemical reagents in such a manner so as to allow their interaction at the molecular level to achieve a chemical or physical transformation of at least one chemical reagent.

As used herein, the term "substituted" refers to the replacement of a hydrogen moiety with a non-hydrogen moiety in a molecule or group.

As used herein, the term "leaving group" refers to a moiety that can be displaced by another moiety, such as by nucleophilic attack, during a chemical reaction. Leaving groups are well known in the art and include, for example, halogen, hydroxy, alkoxy, —O(CO)R$^a$, —OSO$_2$—R$^b$, and —Si(R$^c$)$_3$ wherein R$^a$ can be C$_1$-C$_8$ alkyl, C$_3$-C$_7$ cycloalkyl, aryl, heteroaryl, or heterocycloalkyl, wherein R$^b$ can be C$_1$-C$_8$ alkyl, aryl (optionally substituted by one or more halo, cyano, nitro, C$_1$-C$_4$ alkyl, C$_1$-C$_4$ haloalkyl, C$_1$-C$_4$ alkoxy, or C$_1$-C$_4$ haloalkoxy), or heteroaryl (optionally substituted by one or more halo, cyano, nitro, C$_1$-C$_4$ alkyl, C$_1$-C$_4$ haloalkyl, C$_1$-C$_4$ alkoxy, or C$_1$-C$_4$ haloalkoxy), and wherein R$^c$ can be C$_1$-C$_8$ alkyl. Example leaving groups include chloro, bromo, iodo, mesylate, tosylate, trimethylsilyl, and the like.

As used herein, the term "amino protecting group" refers to a non-hydrogen amino substituent that reversibly preserves a reactively susceptible amino functionality while reacting other functional groups on the compound. A "cyclic amino protecting group" refers to an amino protecting group that includes the protected amino moiety in a ring, such as a phthalimido group, or the like. Examples of amino-protecting groups include formyl, acetyl, trityl, trichloroacetyl, chloroacetyl, bromoacetyl, iodoacetyl, and urethane-type blocking groups such as benzyloxycarbonyl, 4-phenyl-benzyloxycarbonyl, 2-methylbenzyloxycarbonyl, 4-methoxy-benzyloxycarbonyl, 4-fluoro-benzyloxycarbonyl, 4-chloro-benzyloxycarbonyl, 3-chloro-benzyloxycarbonyl, 2-chlorobenzyloxycarbonyl, 2,4-dichloro-benzyloxycarbonyl, 4-bromo-benzyloxycarbonyl, 3-bromo-benzyloxycarbonyl, 4-nitro-benzyloxycarbonyl, 4-cyano-benzyloxycarbonyl, t-butoxycarbonyl, 2-(4-xenyl)-isopropoxycarbonyl, 1,1-diphenyleth-1-yloxycarbonyl, 1,1-diphenylprop-1-yloxycarbonyl, 2-phenylprop-2-yloxycarbonyl, 2-(p-tolyl)-prop-2-yloxycarbonyl, cyclopentanyloxycarbonyl, 1-methyl-cyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl (FMOC), 2-(trimethylsilyl)ethoxycarbonyl, allyloxycarbonyl, 1-(trimethylsilylmethyl)prop-1-enyloxycarbonyl, 5-benzisoxalyl-methoxy-carbonyl, 4-acetoxybenzyloxycarbonyl, 2,2,2-trichloroethoxycarbonyl, 2-ethynyl-2-propoxycarbonyl, cyclopropylmethoxycarbonyl, 4-(decycloxy)benzyloxycarbonyl, isobomyloxy-carbonyl, 1-piperidyloxycarbonlyl and the like; benzoylmethylsulfonyl group, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule. In some embodiments, the amino-protecting groups are t-butoxycarbonyl (t-Boc), allyloxycarbonyl and benzyloxycarbonyl (CbZ). In further embodiment, the amino protecting group is an acyl group such as formyl or acetyl. Further examples of amino protecting groups are found in E. Haslam, *Protecting Groups in Organic Chemistry*, (J. G. W. McOmie, ed., 1973), at Chapter 2; T. W. Greene and P. G. M. Wuts, *Protective Groups in Organic Synthesis*, (1991), at Chapter 7; and T. W. Greene and P. G. M. Wuts, *Protective Groups in Organic Synthesis*, 3rd Ed., (1999), at Chapter 7.

As used herein, the phrase "substantially undetectable amount" refers to an amount of compound that is either absent from a composition or present in the composition in an amount that is either not detectable by routine analytical means or is detected in an amount less than about 0.5 mole % compared with the major component of the composition.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, et al., *Protective Groups in Organic Synthesis,* 3rd Ed., Wiley & Sons, 1999, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tektamethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

Supercritical carbon dioxide can also be used as a solvent.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 25° C.) and "reduced temperature" refers to temperatures below room temperature.

The reactions of the processes described herein can be carried out in air or under an inert atomosphere. Typically, reactions containing reagents or products that are substantially reactive with air can be carried out using air-sensitive synthetic techniques that are well known to the skilled artisan.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, methanesulfonic acid, p-toluene sulfonic acid, benzenesulfonic acid, trifluoroacetic acid, propiolic acid, butyric acid, 2-butynoic acid, vinyl acetic acid, pentanoic acid, hexanoic acid, heptanoic acid, octanoic acid, nbnanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional recrystallization (for example, diastereomeric salt resolution) using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds of the invention can also include tautomeric forms, such as keto-enol tautomers. Tautomeric forms can be in equilibrium or sterically locked into one form by appropriate substitution.

The present invention also includes salt forms of the compounds described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents. Lists of suitable salts are found in *Remington's Pharmaceutical Sciences*, 17th ed., Mack Publishing Company, Easton, Pa., 1985, p. 1418, the disclosure of which is hereby incorporated by reference in its entirety.

Upon carrying out preparation of compounds according to the processes described herein, the usual isolation and purification operations such as concentration, filtration, extraction, solid-phase extraction, recrystallization, chromatography, and the like may be used, to isolate the desired products.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Preparation of 3-dimethylamino-1-(2'-methoxy-5'-acetamidophenyl)prop-2-en-1-one (4)

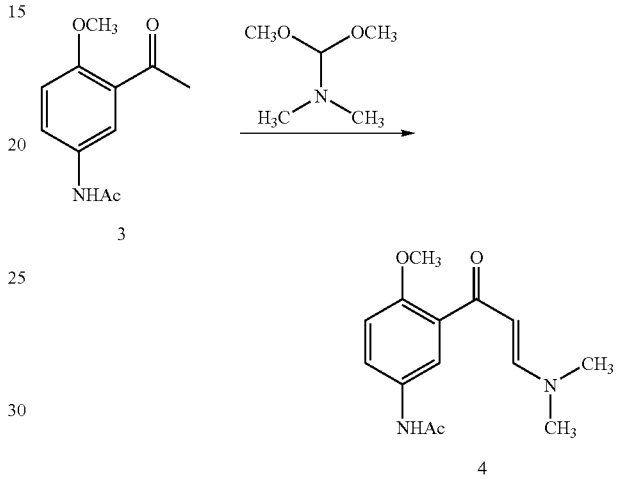

Dimethylformamide dimethyl acetal (693.3 g) was added to a suspension of 2'-methoxy-5'-acetamidoacetophenone (3, 1215.1 g) in ethanol (12.15 L) stirred under nitrogen at 22° C. After the resulting suspension had been stirred and refluxed under nitrogen for 18 hours, all solids had dissolved, and additional dimethylformamide dimethyl acetal (346.2 g) was added to the homogeneous reaction mixture. Stirring and refluxing under nitrogen were continued for an additional 30 hours, after which additional dimethylformamide dimethyl acetal (346.2 g) was added. The reaction mixture was then stirred and refluxed under nitrogen for a final 17.5 hours, after which the reaction mixture was rotary evaporated at <45° C. and <50 mm HgA to a solid residue that was dried further overnight at <45° C. and <1 mm HgA to provide brown solid 4 (1547.9 g, 100.6% yield). LC/MS analyses revealed 98.3% and 100% conversion of 3 to 4 before and after evaporation of solvent, respectively.

Example 2

Preparation of 5-(2'-methoxy-5'-acetamidophenyl)-1-methyl-1H-pyrazole (5)

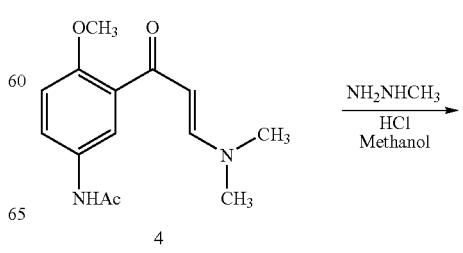

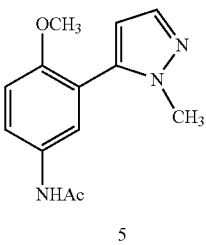

5

Methylhydrazine (319.3 g) was added to methanol (13.931 L) stirred and chilled to −15° C. under nitrogen. Aqueous HCl (37 wt %, 1859.6 g) was then added at a rate sufficiently slow to enable the stirred solution to be maintained at −12 to −7° C. with reactor jacket cooling. As stirring under nitrogen was continued at −10° C., 3-dimethylamino-1-(2'-methoxy-5'-acetamidophenyl)prop-2-en-1-one (4, 1546.9 g) was added as a solid over ten minutes. The resulting homogenous dark brown solution was stirred under nitrogen first at 0° C. for 3 hours and then at 10° C. for 5.5 hours before 33% aqueous ammonia (1090 mL) was added at a rate sufficiently slow (25 minutes) to enable the stirred solution to be maintained at 8.6-15.2° C. with reactor jacket cooling. LC/MS analyses of the reaction mixture before aqueous ammonia treatment revealed 97.3% conversion of 4 to 5 and its other N-methylpyrazole isomer (in 83.3:13.2 ratio) and, after aqueous ammonia treatment, 100% conversion of 4 to 5 and its other N-methylpyrazole isomer (in 87.8:12.2 ratio). The aqueous ammonia addition raised the reaction mixture pH to 8. Methanol (ca. 12 L) was then distilled off the stirred reaction mixture at atmospheric pressure and internal temperatures rising to 74.4° C. Product crystallization, which started at the end of the distillation, was completed by cooling the reaction mixture to −2° C. and holding that temperature with stirring for 44 hours. LC/MS analysis of the crystallization mixture's liquid phase revealed 5 and its other N-methylpyrazole isomer in about 1:3 ratio. (Higher ratios of 5:other isomer in the liquid phase jeopardize product yield, and lower ratios jeopardize product purity. In either case, the crystallization can be repeated by heating the stirred mixture back to reflux at atmospheric pressure and, prior to recrystallization, either distilling off more methanol (if the ratio is high) or adding additional methanol (if the ratio is low).) The reaction mixture was filtered by suction, and the filtered solids were washed with 0° C. water (3 L, then 2×500 mL) and dried at 40° C., <1 mm HgA to provide 5 (1157.7 g, 80.0% yield).

Example 3

Preparation of 5-(2'-Methoxy-5'-acetamidophenyl)-4-bromo-1-methyl-1H-pyrazole (6)

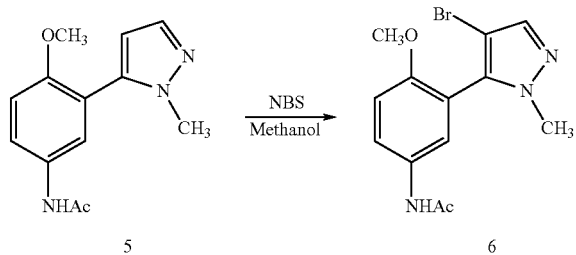

To a solution of 5-(2'-methoxy-5'-acetamidophenyl)-1-methyl-1H-pyrazole (5, 1141.8 g) in methanol (13.75 L) stirred under nitrogen was added solid N-bromosuccinimide (911.5 g) portionwise at a rate sufficiently slow to enable the reaction mixture to be maintained at 13.5-22.5° C. with reactor jacket cooling. Bromopyrazole 6 started to precipitate about three-quarters the way through the addition, which took about 20 minutes to complete. After 30 minutes of continued stirring at 22° C., LC/MS analysis of the reaction slurry revealed complete conversion of 5 to 6; there was no detectable starting material 5. The stirred reaction mixture was then distilled to substantial dryness at 10 mm HgA and internal temperatures up to 30° C. The resulting solid residue was broken up, slurried in a solution of sodium hydroxide (482.25 g) in water (11.538 L) at 25° C. for one hour to remove succinimide byproduct, filtered by suction, washed with water (2×1000 mL), and dried at 22° C. and ca. 10 mm HgA to provide 6 (1385.7 g, 91.8% crude yield) containing ca. 3.2 mole % 5 as the only significant impurity.

Example 4

Preparation of 5-(2'-methoxy-5'-aminophenyl)-4-bromo-1-methyl-1H-pyrazole (7)

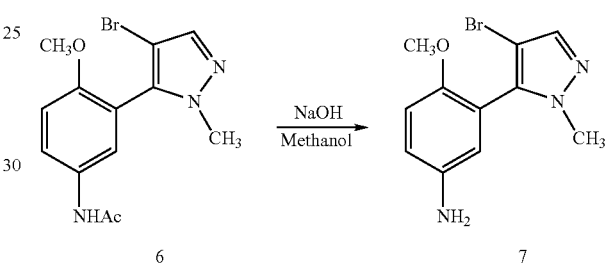

The 5-(2'-methoxy-5'-acetamidophenyl)-4-bromo-1-methyl-1H-pyrazole (6, 1385.7 g) from the previous example, which was contaminated with ca. 3.2 mole % 5, was slurried in methanol (13.3 L) at 22° C. under nitrogen. To the resulting suspension stirred at 22° C. under nitrogen was added solid N-bromosuccinimide (136.7 g total) in three portions. The first portion of N-bromosuccinimide (68.3 g) left ca. 2.8 mole % unreacted 5 after 80 minutes. Then the second portion of N-bromosuccinimide (34.2 g) left ca. 1.8 mole % unreacted 5 after an additional 60 minutes. Then, after the third portion of N-bromosuccinimide (34.2 g) was added, conversion of 5 to 6 was complete within 15 minutes. There was no detectable starting material 5. Aqueous sodium hydroxide (50 wt %; 2606.8 g) was then added to the stirred suspension of 6 over 35 minutes at a rate sufficiently slow to enable the reaction mixture to be maintained at 10.4-24° C. with reactor jacket cooling. After the addition of aqueous sodium hydroxide, a reaction mixture sample was found to contain debrominated 5 in about 2.5 mole % of the amount of 6. Methanol (about 12 L) was then distilled off the stirred reaction mixture over eight hours at 10 mm HgA and internal temperatures rising to 84° C. LC/MS analysis of the reaction mixture, now about 5.5 L of a thick but stirrable suspension, showed complete hydrolysis of 6 to 7 plus about 2 mole % of the desbromo analog of 7. Removal of substantially all remaining methanol (about 1.6 L) by continued distillation over four hours at 10 mm HgA and internal temperatures rising to 55° C. left an unstirrable residue. Upon addition of diisopropyl ether (12 L) and water (1000 mL) and heating to 65° C., the mixture became stirrable, and the solids dissolved completely to provide two liquid phases. The lower (aqueous) phase was drained from the upper (organic) phase, which was then extracted with additional water (1000 mL). The aqueous phases were combined and extracted with more diisopropyl ether (4 L). After extraction with water (1000 mL), the second upper (organic) phase was combined with the first, and the resulting mixture was reheated to 50° C. to completely dissolve all solids. The resulting diisopropyl ether solution was then cooled to −5° C. with stirring over seven hours, during which time 7 crystallized. After being stirred at −5° C. for five more hours, the resulting suspension was filtered by suction. The filtered solid was washed with 0° C. diisopropyl ether (1.0 L) and dried at 40° C. and <1 mm HgA to provide 7 (979.6 g, 81.2 % yield) of 99.2% purity by HPLC with ca. 0.3 wt % desbromo 7 as the largest impurity. The crystallization and wash liquors were combined and evaporated first at 69° C. and atmospheric pressure to 1 L volume and then at <40° C. and 10 mm HgA on a rotary evaporator to provide a residue of pale yellow solid 7 (151.49 g, 12.6% yield) of 94.3% purity by HPLC with ca. 3.5 wt % desbromo 7 as the largest impurity.

Example 5

N-(2,4-Difluorophenyl)-N'-(4-methoxy-3-(4'-bromo-1'-methyl-1H-pyrazol-5'-yl)phenyl)urea (8)

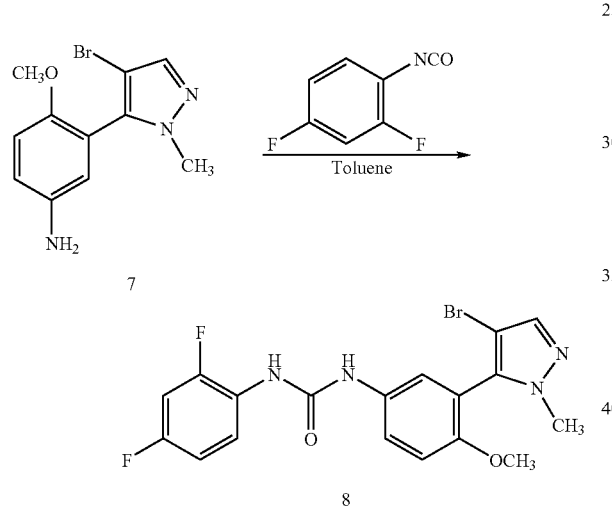

Both portions of 5-(2'-methoxy-5'-aminophenyl)-4-bromo-1-methyl-1H-pyrazole (2) from the previous example were combined by dissolution in toluene (15 L) at 27.6° C., suction filtration of the resulting solution, and rotary evaporation of the filtrate at <50° C. and 10 mm HgA to a constant weight of 1127.0 g. A solution of 7 (1102.0 g of the 1127.0 g evaporation residue) in toluene (11.02 L) was stirred and refluxed at atmospheric pressure through a Dean-Stark trap under nitrogen to remove 0.8 mL of water. After the condensate had become completely clear with no further accumulation of water in the Dean-Stark trap, the toluene solution was cooled under nitrogen to 12.9° C. To the resulting solution stirred under nitrogen was added 2,4-difluorophenyl isocyanate (617.9 g) by addition funnel over 40 minutes at a rate sufficiently slow to enable the reaction mixture to be maintained at 12.9-19° C. with reactor jacket cooling. Solid started to precipitate in the reaction mixture about half way through the addition. After the addition had been completed, the reaction slurry continued to be stirred at 16° C. under nitrogen. Conversion of 7 to 8 was 90%, 91.2%, and 92.6% five, 60, and 120 minutes, respectively, after the addition had been completed. Three hours after the addition had been completed, a second portion of 2,4-difluorophenyl isocyanate (24.4 g) was added, and, after continued stirring of the reaction mixture at 16° C. under nitrogen for an additional 30 minutes, conversion of 7 to 8 was 94%. One hour after the second addition, a third portion of 2,4-difluorophenyl isocyanate (9.7 g) was added, and, after continued stirring of the reaction mixture at 16° C. under nitrogen for an additional 15 minutes, conversion of 7 to 8 was 95%. The reaction mixture was then stirred at 20° C. under nitrogen for an additional 14.75 hours, after which conversion of 7 to 8 was 100%. The reaction mixture was suction filtered, and the filtered solid was washed with 2.6° C. toluene (2×1100 mL) and dried at 100° C. and pressures falling to 1 mm HgA to provide 8 (1654.9 g, 96.9% yield) of 98.2% purity by HPLC with ca. 0.9 mole % desbromo 8 as the largest impurity.

Example 6

Preparation of N-(4-Chlorophenyl)-N'-(4-methoxy-3-(4'-bromo-1'-methyl-1H-pyrazol-5'-yl)phenyl)urea (9)

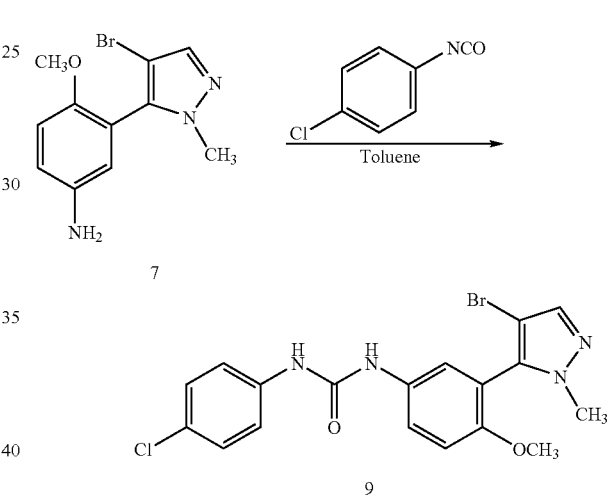

A solution of 7 (101.9 g, 0.3612 mole) in toluene (1020 mL) was stirred and refluxed at atmospheric pressure through a Dean-Stark trap under nitrogen to remove 0.5 mL of water. After the condensate had become completely clear with no further accumulation of water in the Dean-Stark trap, the toluene solution was cooled to ambient temperature, filtered to remove small amounts of insoluble debris, and returned to the reaction flask. While the azeotropically dried toluene solution of 7 was cooled with a water bath and stirred with an overhead stirrer under nitrogen, 4-chlorophenyl isocyanate (55.5 g, 0.3614 mole) was added as a solid in three roughly equal portions. Addition of the first portion over about two minutes caused the reaction mixture temperature to rise from 18.5° C. to 23.5° C. After the reaction mixture had been cooled to 18.7° C., the next two portions of 4-chlorophenyl isocyanate were added over about five minutes without change in reaction mixture temperature. During addition of the first portion, a second (lower) liquid phase separated from the toluene phase. Five minutes after the addition of the last portion had been completed, that second (lower) liquid phase started to crystallize, causing the reaction mixture temperature to rise to 22.5° C. over the next ten minutes. The reaction mixture was stirred at ambient temperature) under nitrogen for 2.5 more hours and then suction filtered. The filtered solid was washed with toluene (150 mL, ambient temperature) and dried at 97° C. and pressures falling to 1 mm HgA over 28 hours to provide 9 (150.08 g, 95.3% yield) containing 1.0 mole % desbromo 9 as the only impurity detectable by $^1$H-NMR and LC/MS analyses.

This application is related to U.S. Provisional Patent Application Ser. No. 60/555,626 filed Mar. 23, 2004 which is incorporated by reference in its entirety.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A process for preparing a compound of Formula (I):

[Structure of Formula (I)]

wherein:
$R^{1a}, R^{1b}, R^{1c}, R^{1d}$, and $R^{1e}$ are each, independently, H, F, or Cl;
$R^2$ is methyl;
$R^3$ is Cl or Br;
$R^4$ is methoxy;
$R^5$, at each occurrence, is H;
the process comprising:
a) reacting a compound of Formula (II):

[Structure of Formula (II)]

with a compound of Formula (III):

[Structure of Formula (III)]

wherein Z is an isocyanate group (—NCO) or isocyanate equivalent to form said compound of Formula (I); or
b) reacting a compound of Formula (II) with an isocyanate-generating reagent to form a compound of Formula (IIa):

[Structure of Formula (IIa)]

wherein Y is an isocyanate group or isocyanate equivalent; and reacting said compound of Formula (IIa) with a compound of Formula (IIIa):

[Structure of Formula (IIIa)]

to form said compound of Formula (I).

2. The process of claim 1 wherein;
$R^{1a}$ is F;
$R^{1b}$ is H;
$R^{1c}$ is F;
$R^{1d}$ is H;
$R^{1e}$ is H;
$R^2$ is methyl;
$R^3$ is Br;
$R^4$ is methoxy; and
$R^5$, at each occurrence, is H.

3. The process of claim 1 wherein:
$R^{1a}$ is H;
$R^{1b}$ is H;
$R^{1c}$ is Cl;
$R^{1d}$ is H;
$R^{1e}$ is H;
$R^2$ is methyl;
$R^3$ is Br;
$R^4$ is methoxy; and
$R^5$, at each occurrence, is H.

4. The process of claim 1 wherein the process comprises reacting a compound of Formula (II):

[Structure of Formula (II)]

with a compound of Formula (III):

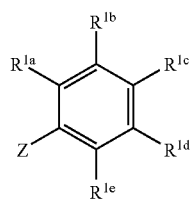

wherein Z is an isocyanate group to form said compound of Formula (I).

5. The process of claim 4 wherein said reacting is carried out in an organic solvent.

6. The process of claim 5 wherein said organic solvent comprises an aromatic solvent.

7. The process of claim 5 wherein said organic solvent comprises toluene.

8. The process of claim 5 wherein said reacting is carried out at a reduced temperature.

9. The process of claim 8 wherein said reduced temperature is about 10 to about 20° C.

10. The process of claim 5 wherein said compound of Formula (III) is added in molar excess relative to the amount of Formula (II).

11. The process of claim 1 wherein said compound of Formula (II) is prepared by the process comprising deprotecting a compound of Formula (IV):

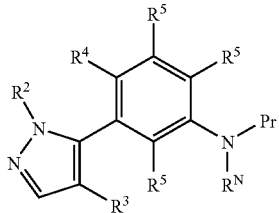

wherein:
Pr is an amino protecting group; and
$R^N$ is H;
or Pr and $R^N$ together with the N atom to which they are attached form a cyclic amino protecting group;
with a deprotecting agent to form said compound of Formula (II).

12. The process of claim 11 wherein said compound of Formula (IV) is prepared by the process comprising halogenating a compound of Formula (V):

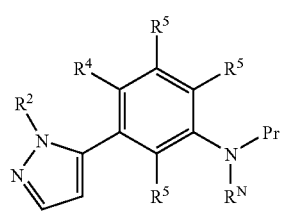

with a halogenating reagent selected from a chlorinating reagent and a brominating reagent to form said compound of Formula (IV).

13. The process of claim 12 wherein said compound of Formula (V) is prepared by the process comprising cyclizing a compound of Formula (VI):

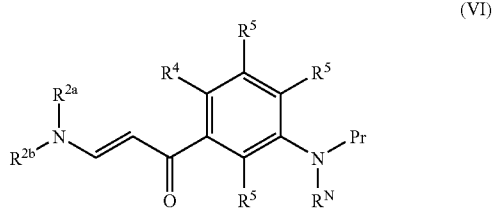

wherein $R^{2a}$ and $R^{2b}$ are each, independently, $C_{1-4}$ alkyl, with an alkylhydrazine having the formula $NH_2NH-R^2$ to form said compound of Formula (V).

14. The process of claim 13 wherein said compound of Formula (VI) is prepared by the processes comprising condensing a compound of Formula (VII):

(VII)

Me─C(=O)─[phenyl with $R^4$, $R^5$, $R^5$, $R^5$]─N(Pr)($R^N$)

with an acetal of Formula (VIII):

(VIII)

R'O─CH(OR)─N($R^{2a}$)($R^{2b}$)

wherein R and R' are each, independently, $C_{1-6}$ akyl, arylalkyl or alkylaryl, or R and R' together with the O atoms to which they are attached and the intervening CH group form a 5- or 6-membered heterocycloalkyl group to form said compound of Formula (VI).

15. A process for preparing a compound of Formula (II):

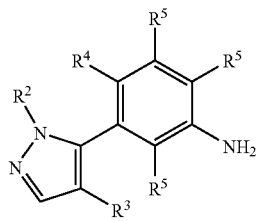

wherein:
$R^2$ is methyl;
$R^3$ is Cl or Br;
$R^4$ is methoxy;

R⁵, at each occurrence, is H;
comprising reacting a compound of Formula (IV):

(IV)

wherein:
Pr is an amino protecting group; and
R^N is H;
or Pr and R^N together with the N atom to which they are attached form a cyclic amino protecting group;
with a base to form said compound of Formula (II).

16. The process of claim 15 wherein Pr is an acyl group.

17. The process of claim 15 wherein Pr is —C(O)Me.

18. The process of claim 15 wherein said base is sodium hydroxide.

19. The process of claim 15 wherein said reacting is carried out in an organic solvent.

20. The process of claim 19 wherein said organic solvent comprises an alcohol.

21. The process of claim 20 wherein said organic solvent comprises methanol.

22. A process for the preparation of a compound of Formula (IV):

(IV)

wherein:
R² is methyl;
R³ is Cl or Br;
R⁴ is methoxy;
R⁵, at each occurrence, is H;
Pr is an amino protecting group; and
R^N is H;
or Pr and R^N together with the N atom to which they are attached form a cyclic amino protecting group;
comprising reacting a compound of Formula (V):

(V)

with a reagent selected from a chlorinating reagent and a brominating reagent to form said compound of Formula (IV).

23. The process of claim 22 wherein said halogenating reagent is a brominating reagent.

24. The process of claim 23 wherein said halogenating reagent comprises N-bromosuccinimide.

25. The process of claim 24 wherein said reacting is carried out in an organic solvent.

26. The process of claim 25 wherein said organic solvent comprises an alcohol.

27. The process of claim 26 wherein said organic solvent comprises methanol.

28. A process for preparing a compound of Formula (V):

(V)

wherein:
R² is methyl;
R³ is Cl or Br;
R⁴ is methoxy;
R⁵, at each occurrence, is H;
Pr is an amino protecting group; and
R^N is H;
or Pr and R^N together with the N atom to which they are attached form a cyclic amino protecting group;
comprising reacting a compound of Formula (VI):

(VI)

wherein $R^{2a}$ and $R^{2b}$ are each, independently, $C_{1-4}$ alkyl, with an alkylhydrazine having the formula $NH_2NH—R^2$ to form said compound of Formula (V).

29. The process of claim 28 wherein said reacting is carried out in the presence of an organic solvent.

30. The process of claim 29 wherein said organic solvent comprises an alcohol.

31. The process of claim 29 wherein said organic solvent comprises methanol.

32. The process of claim 28 wherein said reacting is carried out in the presence of an acid.

33. The process of claim 32 wherein said acid comprises HCl.

34. A compound of Formula (IV) or (V):

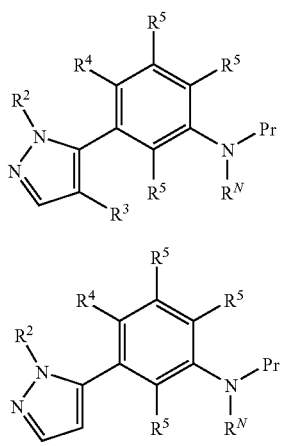

wherein:
R² is methyl;
R³ is Cl or Br;
R⁴ is methoxy;
R⁵, at each occurrence, is H;
Pr is an amino protecting group;
R$^N$ is H; and
or Pr and R$^N$ together with the N atom to which they are attached form a cyclic amino protecting group.

35. The compound of claim 34 wherein said compound has Formula (IV) and R² is methyl; R³ is Br; R⁴ is methoxy; R⁵, at each occurrence, is H; and Pr is —C(O)Me.

36. The compound of claim 34 wherein said compound has Formula (V) and R² is methyl; R⁴ is methoxy; R⁵, at each occurrence, is H; and Pr is —C(O)Me.

37. The process of claim 19 wherein said reacting is carried out at about 0 to about 100° C.

* * * * *